US005612185A

United States Patent [19]
Uhr et al.

[11] Patent Number: 5,612,185
[45] Date of Patent: Mar. 18, 1997

[54] METHOD FOR IDENTIFYING TUMOR CELLS IN CELL CYCLE ARREST

[75] Inventors: Jonathan W. Uhr; Ellen S. Vitetta; Louis J. Picker, all of Dallas; Richard H. Scheuermann, Carrollton, all of Tex.

[73] Assignee: Board of Regents, The University of Texas System, Austin, Tex.

[21] Appl. No.: 306,525

[22] Filed: Sep. 15, 1994

Related U.S. Application Data

[63] Continuation of Ser. No. 967,072, Oct. 14, 1992, abandoned.

[51] Int. Cl.$^6$ .................................................. G01N 33/574
[52] U.S. Cl. .................. 435/7.23; 435/973; 436/538; 436/64; 436/172; 436/813
[58] Field of Search .................. 435/7.23, 968, 435/973; 436/536, 548, 64, 172, 813, 805, 824, 538

[56] References Cited

PUBLICATIONS

Dyke et al., "Idiotypic Vaccination Against B–Cell Lymphoma Leads to Dormant Tumour," *Cell. Immunol.*, 132:70–83, 1991.
George and Stevenson, "Prospects for the Treatment of B Cell Tumors Using Idiotypic Vaccination," *Intern. Rev. Immunol.*, 4:271–310, 1989.
Stevenson et al., "Anti–Idiotypic Therapy of Leukemias and Lymphomas," In: 'Idiotypes in Biology & Medicine,' vol. 48, 1990, Carson, Chen & Kipps, Eds., *Chem. Immunol.*, Basel, pp. 126–166.
Wheelock, E. Frederick, "An Overview of Mechanisms Responsible for Tumor Dormancy," *Cellular Immune Mechanisms and Tumor Dormancy*, pp. 1–13, 1992.
Eccles, Suzanne A., "Dormancy in Experimental Solid Tumour Systems," In: *Cellular Immune Mechanisms and Tumor Dormancy*, pp. 27–46, 1992.
Wheelock et al., "Immune Regulation of a Murine T–Cell Lymphoma Dormant State," In: *Cellular Immune Mechanisms and Tumor Dormancy*, pp. 53–65, 1992.
Stevenson et al., "Idiotypic Vaccination Against B–Cell Lymphoma Leads to Dormant Tumour," In: *Cellular Immune Mechanisms and Tumor Dormancy*, pp. 71–80, 1992.

Uhr et al., "Tumor Dormancy in a Murine B Cell Lymphoma," In: *Cellular Immune Mechanisms and Tumor Dormancy*, pp. 85–96, 1992.
Harris and Braun, "Abnormal Immunoregulation and the Tumor Dormant State in Human Cancer," In: *Cellular Immune Mechanisms and Tumor Dormancy*, pp. 261–276, 1992.
Hollinshead et al., "Soluble Tumor Antigens Used in Clinical Trials of Immunotherapy," In: *Cellular Immune Mechanisms and Tumor Dormancy*, pp. 281–313, 1992.
Diamond et al., The Relationship Between Lymphocyte Nuclear Morphology and Cell Cycle Stage in Lymphoid Neoplasia, *American Journal of Hematology*, 11:165–173, 1981.
Lu et al., Cell Cycle Phase–Specific cDNA Libraries Reflecting Phase–Specific Gene Expression of Ehrlich Ascites Cells Growing in Vivo, *Experimental Cell Research*, 174:199–214, 1988.
Uhr et al., Cancer Dormancy: Studies of the Murine BCL$_1$ Lymphoma$_1$, *Cancer Research (Suppl)*, 51:5045–5053, 1991.
Foon, K. A. et al, *Blood* 68(1):1–31 Jul. 1986.
Ryan, D. H. et al, "Improved Detection of Rare CALLA–Positive Cells in Peripheral Blood Using Multiparameter Flow Cytometry" in *J. Immunol Meth.* 74:115–128, 1984.

*Primary Examiner*—James C. Housel
*Assistant Examiner*—Gary Tanigawa
*Attorney, Agent, or Firm*—Arnold, White & Durkee

[57] ABSTRACT

Disclosed are methods for the identification and characterization of tumor cell types present within malignant populations, and novel methods of cancer treatment. Tumor cells in cell cycle arrest have been identified, purified and characterized according to their size, altered morphology, surface phenotype and expression of oncogenes. Tumor cell cycle arrest can be induced in mice lacking an immune system solely upon administration of anti-idiotype antibodies. Methods of manipulating specific signals from the cell surface to alter the malignant phenotype of transformed cells are disclosed, as are methods for either eliminating or specifically maintaining tumor cells in cell cycle arrest.

8 Claims, 7 Drawing Sheets

BCL₁ Tumor in BALB/c Spleen

Dormant BCL₁ in Id-Immune BALB/c Spleen

METHOD FOR IDENTIFYING TUMOR CELLS IN CELL CYCLE ARREST

This application is a continuation of application Ser. No. 07/967,072, filed Oct. 14, 1992, now abandoned.

BACKGROUND OF THE INVENTION

1. Field of the Invention

The present invention relates generally to immunology and to methods for the diagnosis and treatment of cancer. Disclosed are methods for characterizing distinct sub-sets of tumor cells from within a tumor population, and novel methods of cancer treatment based upon the nature of the cell types identified. In particular, the present invention relates to the identification of tumor cells that are in cell cycle arrest, and to methods for either the elimination or maintenance of such cell cycle arrested populations.

2. Description of the Related Art

The relationship between malignant tumors and their host can be divided into three broad categories: first, continuous growth of the tumor resulting in death of the host; second, complete eradication of tumor cells by natural mechanisms or therapy; and third, a prolonged quiescent state in which tumor cells are present but tumor growth is not clinically apparent. Viable tumor cells which remain present in their host, under some form of growth restraint, can be said to be 'arrested' or to exhibit the phenomenon of tumor dormancy. The existence of such dormant cells can be demonstrated by the eventual growth of a tumor in the host, or, in animal models, by the transfer of tumor to naive recipients.

In human subjects, neoplastic cells are believed to escape from a primary tumor very early in its development. The fate of these escaping neoplastic cells will usually determine the prognosis of the patient. In many cases, tumor cells may remain clinically undetectable for several years. However, this type of micrometastasis in which growth does not occur for long periods of time, frequently ends with the re-emergence of the tumor.

There are many examples of tumor recurrence in humans, both at the primary site or at a distant, metastatic site, many years after the removal of the primary neoplasm (Wheelock et al., 1981). Clinical examples of this include, for example, melanoma and breast carcinoma, where the period of clinical latency can be a decade or more. Indeed, recurrence of breast cancer at the site of surgical incision has been observed after an interval of 50 years (Meltzer, 1990). The phenomenon of waxing and waning of B cell tumors, in the absence of any form of therapy, has also been observed (Krikorian et al., 1980).

An analysis of relapse rates in acute myelogenous leukemia (AML) patients after complete response indicates that relapse can be divided into two phases, an early phase and a late phase, with different relapse rates suggesting that they occur by two different mechanisms. One possible explanation for late relapse is that treatment eliminated the majority of cancer cells, but also altered a small number of cells so that they became resistant and eventually expanded resulting in relapse. If this were the case, the re-emergent tumor would be resistant to the same chemotherapeutic agents. However, this is usually not the case. An alternative explanation is that at the time of therapeutic intervention some of the cancer cells were in a quiescent state. Since most therapeutic agents are effective against dividing cells, the dormant cancer cells would be relatively resistant to treatment, and relapse would be a consequence of these cells subsequently proliferating.

The mechanisms that underlie induction, maintenance, and recurrence of cancers are clearly of great medical importance. Despite such clinical implications, and the fundamental insights that the study of distinct tumor cell populations might give to the biology of cancer and growth control of cells, the topic has received surprisingly little attention, with probably less than 50 experimental studies being published in the last half century. As such, there is no data which currently relates in vitro observations to the more complex situation in vivo. Neither is it known whether dormant cancer cells do not divide, or whether they continue to divide and are killed at the same rate.

A variety of mechanisms, both immunological and non-immunological, have been proposed to be responsible for the long-term behavior of tumor cells. These mechanisms may operate by restraining the tumor cells, or by killing the cells at a rate equal to their division. The eventual escape of tumor cells from a resting, or dormant, stage might be a consequence either of alterations in the host animal, or in the tumor cell, or caused by some interaction between the host and the malignant cells. For example changes in the host's immunological status could allow the tumor to escape from immune control, as could the generation of antigen-negative variant cells. In addition, the vascularization of the tumor, or the movement of neoplastic cells into a site more favorable for their growth, could lead to the breakdown of quiescence (Wheelock et al., 1981).

It is generally believed that cellular immune mechanisms largely control whether tumor cells enter a resting stage as opposed to a growth and reproductive stage. The initiation of dormancy is thought to be a predominantly cytotoxic T-cell mediated process (Weinhold et al., 1979), with longer-term maintenance of this state requiring the further recruitment of macrophages (Robinson & Wheelock, 1981). The re-emergence of tumor cells after a resting period has been reported to be associated with the appearance of macrophages which secrete prostaglandin $E_2$ (Liu et al., 1986), an immunosuppressive factor, as well as, in some cases, selection of variants with reduced antigenicity (Trainer & Wheelock, 1984).

The identification, isolation and characterization of distinct cell types from within a tumor cell population would likely lead to significant advances in our understanding of cancer. Information regarding the characteristics of dormant or quiescent tumor cells would be of great value clinically, creating new possibilities for therapeutic intervention. The development of PCR technology which has facilitated detection of minimal residual diseases in humans, adds impetus to identify and characterize different tumor cell types in order to develop new treatment strategies for cancer patients.

SUMMARY OF THE INVENTION

The present invention addresses one or more of the disadvantages in the prior art by providing novel approaches for the diagnosis, characterization and treatment of cancer. The invention is based generally on the use of immunological agents to identify tumor cells in a resting state and the characterization of such cells as being in cell cycle arrest. This invention further encompasses novel therapeutic strategies for the treatment of cancer, including methods to induce or maintain a state of arrest to prevent tumor growth or metastasis, or alternatively, methods to eliminate tumor cells which are in cell cycle arrest, to allow more complete recovery.

Tumor dormancy is an operational term, which when employed correctly, describes a prolonged quiescent state in which tumor cells are present, but tumor progression is not clinically apparent. Prior to the present invention, it was unknown whether dormant cancer cells divide at a rapid rate and are killed at the same rate, or alternatively, do not divide. Moreover, the general phrases dormant and dormancy are often erroneously used in the art with a wide variety of meanings. A key discovery of this invention is the finding that tumor cells previously referred to as 'dormant' are in a state of cell cycle arrest. Thus dormancy, which was strictly an operational definition before this invention, has now been given a cellular definition.

To clearly differentiate this newly and precisely defined tumor cell type from the general phrases dormant and dormancy, the terms cell cycle arrest, cell cycle-arrested cells (CCAC), cell cycle-arrested lymphoma cells (CCALC), or simply the term 'arrested', will be employed herein to refer to that population of tumor cells which have been cellularly and molecularly defined as dormant.

The present invention concerns, firstly, methods for characterizing cancers or tumors by analyzing a population of cells derived therefrom. The analysis and characterization of cancer or tumor cells is important in that it allows optimal therapeutic strategies directed to the specific cancer to be designed and employed. In particular, the present invention concerns the identification of tumor cells which may be characterized as dormant, i.e., which are in a resting or quiescent state.

To characterize a cancer or tumor in this manner one would firstly obtain a population of tumor cells from a patient suspected of having cancer, for example, from a biological specimen such as a biopsy sample. To determine whether the sample contains dormant or quiescent cells, one would then analyze the tumor cell population for the presence of tumor cells in cell cycle arrest. To achieve this, one would firstly separate the tumor cells into distinct populations, preferably by employing multiparameter cell sorting, and then identify arrested tumor cells according to one or more of the criteria disclosed hereinbelow.

In particular, one would identify a tumor cell in cell cycle arrest as having a DNA content corresponding to the $G_0/G_1$ cell cycle stage, or as being of smaller size relative to malignant tumor cells, or more preferably, of exhibiting both of the above properties. One may also identify tumor cells in cell cycle arrest according to their morphology, as arrested tumor cells will typically have an inactive nuclear morphology, such as characterized by the presence of clumped chromatin, or the absence of conspicuous nucleoli.

Suitable techniques of multiparameter cell sorting will be known to those of skill in the art in light of the present disclosure. Generally speaking one contacts the population of tumor cells to be analyzed with a panel of antibodies directed against distinct cell surface molecules, under conditions effective to allow antibody binding. The antibodies employed would preferably be monoclonal antibodies, and would be labelled in a manner to allow their subsequent detection, such as by tagging with a fluorescent label. By using fluorochromes that can be excited by 2 different lasers to give off light at 4 different wavelengths, it is possible to use 4 distinct antibodies to 4 different surface antigens and, in addition, to use 2 light scattering parameters, direct and orthogonal. Thus cells can be sperated on the basis of 6 parameters. The population of tumor cells with bound antibodies may then be separated by cell sorting, preferably using fluorescence-activated flow cytometry.

It is contemplated that the choice of antibodies for use in cell sorting will be governed in general by the type of tumor to be characterized. Naturally, the antibodies employed should be directed against molecules which have epitopes that are accessible to antibody binding, and would thus likely be cell surface molecules. With particular reference to B cell tumors, it is contemplated that one may wish to employ antibodies directed against certain immunological molecules, including for example, immunoglobulin idiotype, CD19, CD20, CD22, CD40, MHC class I and $F_c\gamma IIR$ molecules.

However, as will be discussed more fully below, the methods of the present invention may be employed to tumors of any description. It is contemplated that one would employ antibodies directed against appropriate markers such that cell cycle arrested cells would have a unique physical and antigenic characteristics distinguishing them both qualitatively and quantitatively from other cells within the population and allowing their isolation. Antibodies directed against tumor markers, such as any of those listed in Table I, are contemplated to be of use for identifying and isolating cell cycle arrested cells. In order to identify the presence of, for example, breast tumor cells in the bone marrow, a single antibody directed against a breast-specific tumor antigen may be employed.

In preferred embodiments for multiparameter cell sorting, it is contemplated that one would wish to employ a combination of agents that results in independent signals of 4 different wavelengths. This may be readily achieved by using four distinct monoclonal antibodies. Alternatively, the fourth signal may be supplied by employing a DNA stain which results in color generation, such as Hoechst, and in these circumstances only three monoclonal antibodies may be used in the separation procedure. Whichever combination is used, the objective of the separation is to allow the identification of tumor cells which are generally smaller in size and which are not dividing.

Alternatively, in light of the present invention, a population of tumor cells may be separated into distinct cell types by other means, such as, for example, using methods based upon various cellular characteristics such as size, shape, density, and the like. Suitable alternative separation methods include, for example, differential centrifugation. The option of employing separation methods other than multiparameter cell sorting is a direct result of further aspects of the present invention in which the characteristics of quiescent tumor cells have been precisely defined. Thus cell cycle arrested tumor cells may now, for the first time, be identified from a panel of tumor cells regardless of the isolation methods employed.

Following the separation of distinct tumor cell types, dormant tumor cells may be precisely identified as those tumor cells under cell cycle arrest. Such cells may be defined according to any one of the variety of characteristics disclosed herein to differentiate cell cycle arrested cells from other cells of malignant phenotype. In addition to their DNA content, size and morphology, such characteristics may include, for example, the expression of various genes including cellular protooncogenes.

The DNA content of a cell is known to define its cell cycle status, therefore by determining the cellular DNA content one may determine whether the cell is in $G_0$, $G_1$, $G_2$, S or M stages of the cell cycle. Various methods may be employed to determine the DNA content of a cell, any or all of which are considered to be of use in the present invention. These include, for example, any dye or binding material that indicates the amount of DNA per cell, such as the DNA-binding dye Hoechst 33342, propidiem iodide or bromodeoxyuridine (BrdU). Cell cycle arrested tumor cells may be identified as that population of cells in which the number of cells present in $S+G_2+M$ is significantly reduced, and more preferably, in which the number of cells present in $G_0/G_1$ is significantly increased, with respect to other tumor cell populations.

Important characteristics for identifying tumor cells as tumor cells under cell cycle arrest are size and morphology. The presence of small tumor cells indicates arrested tumor cells and differentiates them from their malignant counterparts. With respect to tumor cell morphology, cell cycle arrested tumor cells may also be identified as those cells which generally have nuclei with an inactive appearance, such as nuclei with clumped chromatin, or nuclei with absent or conspicuous nucleoli.

A further method for characterizing tumor cells as cells under cycle arrest is based upon the expression of certain key genes, such as cellular protooncogenes. For example, it is envisioned that decreased expression of the c-myc gene may be one indication of an arrested cell. More particularly, the increased expression of genes encoding AP1 transcription factors, such as c-jun, and even more particularly, c-fos, is envisioned to be characteristic of cell cycle arrested tumor cells.

The expression of genes which characterize arrested cells, such as AP1 transcription factor genes, may be analyzed by any one of a variety of methods, including determining the levels of specific mRNA or protein. Protein levels may be analyzed by, for example, western blotting with specific antisera, or by measuring the activity of the encoded protein, such as, in the case of transcription factors, by employing DNA gel shift assays or by analyzing the expression of genes known to be activated by such factors. The most straightforward and direct and, therefore, the preferred method of analyzing the expression of a particular gene is to measure the levels of the specific mRNA, for example by Northern blotting with specific probes. The execution of any of the above assays will be known to those of skill in the art in light of the present disclosure.

The characterization and analysis of human tumor cells using the methods of the present invention is considered to be particularly suitable for the analysis of B cell tumors, and preferably, non-Hodgkin's lymphomas, as these most closely resemble the animal model employed in the present studies. However, as with the cell sorting protocol, it should be noted that methods of the present invention may be used to analyze a wide variety of tumors. This is also true for the treatment methods encompassed by the present invention, the wide-ranging applicability of which will be discussed in more detail below.

In further and important embodiments, the present invention concerns the inhibition of tumor cell growth or reproduction, as may be used particularly in the treatment of cancers which are not amenable to standard therapeutic protocols. To inhibit tumor growth, reproduction or progression, including metastasis, in accordance herewith, one would contact the tumor population with a composition capable of inducing the cell cycle arrest of tumor cells.

This approach is contemplated to be particularly suitable for the treatment of animals, including human subjects, with aggressive malignancies. It is envisioned that, through such treatments which induce tumor cell cycle arrest, long-term remissions may be achieved in patients with tumors which had proven resistant to more conventional therapy. To treat patients with such a cancer, one would administer to the patient a composition capable of inducing tumor cell cycle arrest in a pharmacologically acceptable vehicle.

The compositions contemplated for use in such embodiments are those capable of inducing tumor cells to enter the $G_0/G_1$ cell cycle phase, or to maintain cells in this phase, and compositions which favor the generation of small tumor cells or tumor cells with inactive nuclear morphology. In certain embodiments, it is contemplated that such compositions will likely increase the levels of one or more AP1 transcription factors, such as c-jun, or more preferably, c-fos, within the tumor cells, although the cell cycle status and cell size are thought to be the most universally applicable markers of arrested tumor cells.

Compositions capable of achieving this will likely contain a molecule, such as antibody, or even a solubilized T cell receptor fragment, which can interact with a receptor present on the surface of tumor cells. This interaction will preferably lead to initial cross linking of the receptors, although continued cross-linking is not considered to be essential for cell cycle arrest. Accordingly, it is contemplated that where antibodies directed against cell surface receptors are employed, the use of a divalent antibody will be preferred.

With reference to the treatment of B cell tumors, including non-Hodgkin's lymphoma, it is contemplated that antibodies directed against the cell surface Ig, and particularly against the idiotypic tumor marker Ig components, will be particularly useful as cell cycle arrest inducing components. Antibodies directed against Fc receptor and CD19-like molecules are also contemplated to be particularly useful in this regard.

In the most preferred B cell treatment embodiments, it is contemplated that one would wish to avoid specifically stimulating or otherwise contacting certain cell surface molecules which may interfere with or inhibit the induction of cell cycle arrest after receptor cross-linking. Such molecules include, for example, the IL-4 receptor, IgD and even CD40.

The induction of tumor cell cycle arrest in accordance with the present invention, as elucidated using a B cell system, rests upon the manipulation of signal transduction pathways which stem from cell surface receptors. All cells, including tumor cells, contain cell surface molecules which transduce signals from the external environment to the nucleus, thereby affecting gene expression. Therefore the phenomenon of cell cycle arrest, demonstrated in a lymphoid malignancy, may be considered to be generalizable to all forms of malignancy. It is contemplated that tumor cells of any given cell type will express one or more cell surface receptor(s), which when contacted from the external environment, will be able to induce cell cycle arrest, thus rendering the present invention widely applicable to the treatment of any cancer.

All cells express major histocompatibility (MHC) Class I antigens on their surface and some have Class II MHC antigens such as B cells and macrophages. Both classes of MHC molecules function to bind peptides and to present them to distinct classes of T cells, by forming an interaction with specific T cell receptors. One aspect of this invention thus contemplates the use of antigen-specific solubilized T cell receptors as signal transducing agents to effect tumor cell cycle arrest in the cells of any tumor. Alternatively, antibodies that imitate the specificity of the T cell receptor against the peptide that protrudes from the MHC pocket could also be employed.

In preferred embodiments, it is contemplated that cell cycle arrest may be induced in the cells of any type of tumor in response to contacting the cells with a composition comprising antibodies directed against a cell surface tumor marker or antigen. An important aspect of the present invention is the novel demonstration that tumor cell cycle arrest can be induced in SCID mice, which lack an immune system, solely upon administration of such antibodies. Therefore, although the treatment methods of the present invention may be combined with the use of other agents, if desired, it is contemplated that the administration of an antibody composition alone will be advantageous.

As mentioned above, for the treatment of B cell tumors, the use of antibodies directed against epitopes, and particularly idiotypic epitopes, of the surface immunoglobulin (sIg) are preferred. Antibodies against the milk mucin core protein are contemplated to be particularly useful for the treatment of breast tumors. In regard to the treatment of other tumors, a large number of tumor-associated antigens and corresponding antibodies have now been described in the scientific literature, for example, see Table I, any of which are contemplated to be of use in accordance herewith. It will be appreciated that Table I provides an illustrative rather than exhaustive list.

TABLE I

| | TUMOR MARKERS AND CORRESPONDING MONOCLONAL ANTIBODIES | | |
|---|---|---|---|
| Tumor Site | Antigen Identity/ Characteristics | Monoclonal Antibodies | Reference |
| A: Gynecological GY | 'CA 125' >200 kD mucin GP | OC 125 | Kaba,at et al., Int. J. Gynecol. Pathol., 4:265, 1983; Szymendera, Tumour Biology, 7:333, 1986 |
| ovarian | 80 Kd GP | OC 133 | Masuko et al, Cancer Res., 44:2813, 1984 |
| ovarian | 'SGA' 360 Kd GP | OMI | de Krester et al., Int. J. Cancer, 37:705, 1986 |
| ovarian | High $M_r$ mucin | Mo v1 | Miotti et al, Cancer Res., 65:826, 1985 |
| ovarian | High $M_r$ mucin/ glycolipid | Mo v2 | Miotti et al, Cancer Res., 65:826, 1985 |
| ovarian | NS | 3C2 | Tsuji et al., Cancer Res., 45:2358, 1985 |
| ovarian | NS | 4C7 | Tsuji et al., Cancer Res., 45:2358, 1985 |
| ovarian | High $M_r$ mucin | $ID_3$ | Gangopadhyay et al., Cancer Res., 45:1744, 1985 |
| ovarian | High $M_r$ mucin | DU-PAN-2 | Lan et al, Cancer Res., 45:305, 1985 |
| GY | 7700 Kd GP | F 36/22 | Croghan et al., Cancer Res., 44:1954, 1984 |
| ovarian | 'gp 68' 48 Kd GP | $4F_7/7A_{10}$ | Bhattacharya et al., Cancer Res., 44:4528, 1984 |
| GY | 40, 42kD GP | OV-TL3 | Poels et al., J. Natl. Cancer, 76:781, 1986 |
| Gy | 'TAG-72' High $M_r$ mucin | B72.3 | Thor et al., Cancer Res., 46:3118, 1986 |
| ovarian | 300–400 Kd GP | $DF_3$ | Kufe et al., Hybridoma, 3:223, 1984 |
| ovarian | 60 Kd GP | $2C_8/2F_7$ | Bhattacharya et al., Hybridoma, 4:153, 1985 |
| Gy | 105 Kd GP | MF 116 | Mattes et al., PNAS, 81:568, 1984 |
| ovarian | 38–40 kD GP | MOvl8 | Miotti et al., Int. J. Cancer 39:297, 1987 |
| GY | 'CEA' 180 Kd GP | CEA 11-H5 | Wagener et al., Int. J. Cancer, 33:469, 1984 |
| ovarian | CA 19-9 or GICA | CA 19-9 (1116NS 19-9) | Atkinson et al., Cancer Res., 62:6820, 1982 |
| ovarian | 'PLAP' 67 Kd GP | H17-E2 | McDicken et al., Br. J. Cancer, 52:59, 1985 |
| ovarian | 72 Kd | 791T/36 | Perkins et al., Eur. J. Nucl. Med., 10:296, 1985 |
| ovarian | 69 Kd PLAP | $NDOG_2$ | Sunderland et al., Cancer Res., 44:4496, 1984 |
| ovarian | unknown $M_r$ PLAP | H317 | Johnson et al., Am. J. Reprod. Immunol., 1:246, 1981 |
| ovarian | $P185^{HER2}$ | 4DS, 3H4, 7C2, 6E9, 2C4, 7F3, 2H11, 3E8, 5B8, 7D3, SB8 | Shepard et al., J. Clin. Immunol., 11(3):117, 1991 |
| uterus ovary | HMFG-2 | HMFG2 | Epenetos et al., Lancet, Nov. 6, 1000–1004, 1982 |
| GY | RMFG-2 | 3.14.A3 | Burchell et al., J. Immunol., 131:508, 1983 |
| B: BREAST | 330–450 Kd GP | DF3 | Hayes et al., J. Clin. envest., 75:1671, 1985 |
| | NS | NCRC-11 | Ellis et al., Histopathol., 8:501, 1984 |
| | 37kD | 3C6F9 | Mandeville et al., Cancer Detect. Prev., 10:89, 1987 |
| | NS | MBE6 | Teramoto et al., Cancer, 50:241, 1982 |
| | NS | CLNHS | Glassy et al., PNAS, 80:63227, 1983 |
| | 47 Kd GP | MAC 40/43 | Kjeldsen et al, 2nd Int. Wkshop of MAbs & Breast Cancer, San Fran., Nov. 1986 |
| | High $M_r$ GP | EMA | Sloane et al., Cancer, 17:1786, 1981 |
| | High $M_r$ GP | HMFG1 HFMG2 | Arklie et al., Int. J. Cancer, 28:23, 1981 |
| | NS | 3.15.C3 | Arklie et al., Int. J. Cancer, 28:23, 1981 |
| | NS | M3, M8, M24 | Foster et al., Virchowe Arch. (Pathol. Anat. Histopathol.), 394:295, 1982 |
| | 1 (Ma) blood group Age | M18 | Footer et al., HumanPathol., 15:502, 1984 |
| | NS | 67-D-11 | Rasmussen et al., Breast Cancer Res. Treat., 2:401, 1982 |

TABLE I-continued

TUMOR MARKERS AND CORRESPONDING MONOCLONAL ANTIBODIES

| Tumor Site | Antigen Identity/ Characteristics | Monoclonal Antibodies | Reference |
|---|---|---|---|
| | oestrogen receptor | D547Sp, D75P3, H222 | Kinsel et al., Cancer Res., 49:1052, 1989 |
| | EGF Receptor | Anti-EGF | Sainabury et al, Lancet, 1:364, 1985 |
| | Laminin Receptor | LR-3 | Horan Hand et al., Cancer Res., 45:2713, 1985 |
| | erb B-2 p185 | TA1 | Guaterson et al., Br. J. Cancer, 58t453, 1988 |
| | NS | H59 | Hendler et al., Trans. Assoc. Am. Physicians, 94:217, 1981 |
| | 126 Kd GP | 10-3D-2 | Soule et al., PNAS, 80:2332, 1983 |
| | NS | HmAB1, 2 | Imam et al., cited in Schlom et al., Adv. Cancer Res., 43:143, 1985 |
| | NS | MBR 1, 2, 3 | Menard et al., Cancer Res., 63:1295, 1983 |
| | 95 Kd | 24 · 17 · 1 | Thompson et al., J. Natl. Cancer Inst., 70:409, 1983 |
| | 100 Kd | 24 · 17 · 2 (3E1 · 2) | Croghan et al., Cancer Res., 43:4980, 1983 |
| | NS | P36/22.M7/105 | Croghan et al., Cancer Res., 44:1954, 1984 |
| | 24 Kd | C11, G3, H7 | Adams et al., Cancer Res., 43:6297, 1983 |
| | 90 Kd GP | B6 · 2 | Colcher et al., PNAS, 78:3199, 1981 |
| | CEA & 180 Kd GP | B1 · 1 | Colcher et al., Cancer Invest., 1:127, 1983 |
| | colonic & pancreatic mucin similar to Ca 19-9 | Cam 17.1 | Imperial Cancer Research Technology Mab listing |
| | milk mucin core protein | SM3 | Imperial Cancer Research Technology Mab listing |
| | milk mucin core protein | SM4 | Imperial Cancer Research Technology Mab listing |
| | affinity-purified milk mucin | C-Mul (566) | Imperial Cancer Research Technology Mab listing |
| | p185$^{HER2}$ | 4D5 3H4, 7C2, 6E9, 2C4, 7F3, 2H11, 3E8, 5B8, 7D3, 5B* | Shepard et al., J. Clin. Immunol., 11(3):117, 1991 |
| | CA 125 >200 Kd GP | OC 125 | Kabawat et al., Int. J. Gynecol. Pathol., 4:245, 1985 |
| | High $M_r$ mucin/ glycolipid | MO v2 | Miotti et al., Cancer Res., 45:826, 1985 |
| | High $M_r$ mucin | DU-PAN-2 | Lan et al., Cancer Res., 44:1954, 1984 |
| | 'gp48' 48 Kd GP | 4F$_7$/7A$_{10}$ | Bhattacharya et al., Cancer Res., 44:4528, 1984 |
| | 300-400 Kd GP | DF$_3$ | Kufe et al., Hybridoma, 3:223, 1984 |
| | 'TAG-72' high $M_r$ mucin | B72.3 | Thor et al., Cancer Res., 46:3118, 1986 |
| | 'CEA' 180 Kd GP | cccccCEA 11 | Wagener et al., Int. J. Cancer, 33:469, 1984 |
| | 'PLAP' 67 Kd GP | H17-E2 | McDicken et al., Br. J. Cancer, 52:59, 1985 |
| | HMFG-2 >400 Kd GP | 3 · 14 · A3 | Burchell et al., J. Immunol., 131:508, 1983 |
| | NS | F023C5 | Riva et al., Int. J. Cancer, 2:114, 1988 (Suppl.) |
| C: COLORECTAL | TAG-72 High $M_r$ mucin | B72 · 3 | Colcher et al., Cancer Re$., 47:1185 & 4218, 1987 |
| | GP37 | (17-1A) 1083-17-IA | Paul et al., Hybridoma, 5:171, 1986 |
| | Surface GP | CO17-1A | LoBuglio et al., JNCl, 80:932, 1988 |
| | CEA | ZCE-025 | Patt et al., Cancer Bull., 40:218, 1988 |
| | CEA | AB2 | Griffin et al., Proc. 2nd Conf. on Radioimmunodetection & Therapy of Cancer, 82, 1988 |
| | cell surface AG | HT-29-15 | Cohn et al., Arch. Surg. 122:1425, 1987 |
| | secretory epithelium | 250-30.6 | Leydem et al., Cancer, 57:1135, 1986 |
| | surface glycoprotein | 44X14 | Gallagher et al., J. Surg. Res., 40:159, 1986 |
| | NS | A7 | Takahashi et al., Cancer, 61:881, 1988 |
| | NS | GA73 · 3 | Munz et al., J. Nucl, Med., 27:1739, 1986 |
| | NS | 791T/36 | Farrans et al., Lancet, 2:397, 1982 |
| | cell membrane & cytoplasmic Ag | 28A32 | Smith et al., Proc. Am. Soc. Clin. 0. col., 6:250, 1987 |
| | CEA & vindesine | 28.19.8 | Corvalen, Cancer Immuno., 24:133, 1987 |
| | gp72 | X MMCO-791 | Byers et al., 2nd Int. Conf. Mab Immunocon. Cancer, 41:1987 |
| | high $M_r$ mucin | DU-PAN-2 | Lan et al., Cancer Res., 45:305, 1985 |
| | high $M_r$ mucin | ID$_3$ | Gangopadhyay et al., Cancer Res., 45:1744, 1985 |

TABLE I-continued

TUMOR MARKERS AND CORRESPONDING MONOCLONAL ANTIBODIES

| Tumor Site | Antigen Identity/ Characteristics | Monoclonal Antibodies | Reference |
|---|---|---|---|
| | CEA 180 Kd Gp | CEA 11-H5 | Wagener et al., Int. J. Cancer, 33:469, 1984 |
| | 60 Kd GP | $2C_8/2F_7$ | Bhattacharya et al., Hybridoma, 4:153, 1985 |
| | CA-19-9 (or GICA) | CA-19-9 (1116NS 19-9) | Atkinson et al., Cancer Res., 62:6820, 1982 |
| | Lewis a | PR5C5 | Imperial Cancer Research Technology Mab Listing |
| | Lewis a | PR4D2 | Imperial Cancer Research Technology Mab Listing |
| | colonic mucus | PR4D1 | Imperial Cancer Research Technology Mab Listing |
| D: MELANOMA | $p97^a$ | 4 · 1 | Woodbury et al., PNAS, 77:2183, 1980 |
| | $p97^a$ | 8 · 2 $M_{17}$ | Brown, et al., PNAS, 78:539, 1981 |
| | $p97^b$ | 96 · 5 | Brown, et al., PNAS, 78:539, 1981 |
| | $p97^c$ | 118.1, 133.2, (113 · 2) | Brown, et al., PNAS, 78:539, 1981 |
| | $p97^c$ | $L_1, L_{10}, R_{10}(R_{19})$ | Brown et al., J. Immunol., 127:539, 1981 |
| | $p97^d$ | $I_{12}$ | Brown et al., J. Immunol., 127:539, 1981 |
| | $p97^e$ | $K_5$ | Brown et al., J. Imunol., 127:539, 1981 |
| | p155 | 6 · 1 | Loop et al., Int. J. Cancer, 27:775, 1981 |
| | $G_{D3}$ disialoganglioside | R24 | Dippold et al., PNAS, 77:6115, 1980 |
| | P210, p60, p250 | 5 · 1 | Loop et al., Int. J. Cancer, 27:775, 1981 |
| | P280 p440 | 225.28S | Wilson et al., Int. J. Cancer, 28:293, 1981 |
| | GP 94, 75, 70 & 25 | 465.12S | Wilson et al., Int. J. Cancer, 28:293, 1981 |
| | P240—P250, P450 | 9 · 2 · 27 | Reisfeld et al., Melanoma Ago & Abo, 1982 pp. 317 - |
| | 100, 77, 75 Kd | F11 | Chee et al., Cancer Res., 42:3142, 1982 |
| | 94 Kd | 376.96S | Imai et al., JNCI, 68:761, 1982 |
| | 4 GP chains | 465.12S | Imai et al., JNCI, 68:761, 1982; Wilson et al., Int. J. Cancer, 28:293, 1981 |
| | GP 74 | 15 · 75 | Johnson & Reithmuller, Hybridoma, 1:381, 1982 |
| | GP 49 | 15 · 95 | Johnson & Reithmuller, Hybridoma, 1:381, 1982 |
| | 230 Kd | Mel-14 | Carrel et al., Hybridoma, 1:387, 1982 |
| | 92 Kd | Mel-12 | Carrel et al., Hybridoma, 1:387, 1982 |
| | 70 Kd | Me3-TB7 | Carrel et al., Hybridoma, 1:387, 1982 |
| | HMW MAA similar to 9 · 2 · 27 AG | 225.28SD | Kantor et al., Hybridoma, 1:473, 1982 |
| | HMW MAA similar to 9 · 2 · 27 AG | 763.24TS | Kantor et al., Hybridoma, 1:473, 1982 |
| | GP95 similar to 376 · 96S 465 · 12S | 705F6 | Stuhlmiller et al., Hybridoma, 1:447, 1982 |
| | GP125 | 436910 | Saxton et al., Hybridoma, 1:433, 1982 |
| | CD41 | M148 | Imperial Cancer Research Technology Mab listing |
| E: GASTROINTESTINAL pancreas, stomach gall bladder, | high $M_r$ mucin | ID3 | Gangopadhyay et al., Cancer Res., 45:1744, 1985 |
| pancreas, stomach | high $M_r$ mucin | DU-PAN-2 | Lan et al., Cancer Res., 45:305, 1985 |
| pancreas | NS | OV-TL3 | Poels et al., J. Natl. Cancer Res., 44:4528, 1984 |
| pancreas, stomach, oesophagus | 'TAG-72' high $M_r$ mucin | B72 · 3 | Thor et al., Cancer Res., 46:3118, 1986 |
| stomach | 'CEA' 180 Kd GP | CEA 11-H5 | Wagener et al., Int. J. Cancer, 33:469, |
| pancreas | HMFG-2 >400 Kd GP | 3 · 14 · A3 | Burchell et al., J. Immunol., 131:508, 1983 |
| G · I · | NS | C COLI | Lemkin et al., Proc. Am. Soc. Clin. oncol., 3:47, 1984 |
| pancreas, stomach | CA 19-9 (or GICA) | CA-19-9 (1116NS 19-9) and CA50 | Szymendera, Tumour Biology, 7:333, 1986 |
| pancreas | CA125 GP | OC125 | Szymendera, Tumour Biology, 7:333, 198 |
| F: LUNG non-small cell lung carcinoma | $p185^{HER2}$ | 4D5 3H4, 7C2, 6E9, 2C4 7F3, 2H11, 3E8, 5B8, 7D3, SB8 | Shepard et al., J. Clin. Immunol., 11(3):117, 1991 |
| | high $M_r$ mucin/ glycolipid | Mo v2 | Miolti et al., Cancer Res., 65:826, 1985 |
| | 'TAG-72' high $M_r$ mucin | B72 · 3 | Thor et al., Cancer Roe., 46:3118, 1986 |
| | high $M_r$ mucin | DU-PAN-2 | Lan et al., Cancer Res., 45:305, 1985 |
| | 'CEA' 180 kD GP | CEA 11-H5 | Wagener et al, Int. J. Cancer., 33:469, 1984 |
| Malignant Gliomas | cell surface Ag | MUC 2-63 | Stavrou, Neurosurg. Rev., 13:7, 1990 |

TABLE I-continued

TUMOR MARKERS AND CORRESPONDING MONOCLONAL ANTIBODIES

| Tumor Site | Antigen Identity/ Characteristics | Monoclonal Antibodies | Reference |
|---|---|---|---|
| | from 85HG-63 cells | | |
| | cell surface Ag from 86HG-39 cells | MUC 2-39 | Stavrou, Neurogurg. Rov., 13:7, 1990 |
| | cell sufface Ag from 86HG-39 cell | MUC 7-39 | Stavrou, Neurosurg. Rev., 13t7, 1990 |
| G: MISCELLANEOUS | p53 | PAb 240 | Imperial Cancer Research Technology MaB Listing |
| | | PAb 246 | |
| | | PAb 1801 | |
| small round cell tumours | neural cell adhesion molecule | ERIC · 1 | Imperial Cancer Research Technology MaB Listing |
| medulloblastoma neuroblastoma rhabdomyosarcoma | | M148 | Imperial Cancer Research Technology MaB Listing |
| neuroblastoma | | FMH25 | Imperial Cancer Research Technology MaB Listing |
| renal cancer & glioblastomas | p155 | 6 · 1 | Loop et al., Int. J. Cancer, 27:77S, 1981 |
| bladder & laryngeal cancers | "Ca Antigen" 350–390 kD | CA1 | Ashall et al., Lancet, July 3, 1, 1982 |
| neuroblastoma | GD2 | 3F8 | Cheung et al., Proc. AACR, 27:318, 1986 |
| Prostate | gp48 48 kD GP | $4F_7/7A_{10}$ | Shattacharya et al., Cancer Rex. 44:4528, 1984 |
| Prostate | 60 kD GP | $2C_8/2F_7$ | Bhattacharya at al., Hybridoma, 4:153, 1985 |
| Thyroid | 'CEA' 180 kD GP | CEA 11-HS | Wagener et al., Int. J. Cancer, 33:469, 1984 | abbreviations: Abs, antibodies; Ags, antiens; EGF, epidermal growth factor, GI, gastrointestinal; GICA, gastrointestinal-associated antigen; GP, glycoprotein; GY, gynecological; HMPG, human milk fat globule; Kd, kilodaltons; Mabs, monoclonal antibodies; $M_r$, molecular weight; NS, not specified; PLAP, placental alkaline phosphatase; TAG, tumour-associated glycoprotein; CEA, carcinoembryonic antigen.

footnotes: the CA 19-9 Ag (GICA) is sialoaylfucosyllactotetraosylceramide, also termed sialylated Lewis pentaglycosyl ceramide or sialyated lacto-N-fucopentaose II; p97 Age are believed to be chondroitin oulphate proteoglycan; antigens reactive with Mab 9-2-27 are believed to be sialylated glycoproteine associated with chondroitin sulphate proteoglycan; unless specified, GY can include cancers of the cervix, endocervix, endometrium, fallopian tube, ovary, vagina or mixed Mullerian tumour; unless specified GI can include cancers of the liver, small intestine, spleen, pancreas, stomach and oesophague.

Generally speaking, antibodies for use in the present invention will preferably exhibit properties of high affinity, such as exhibiting a $K_d$ in the order of 200–100 nM or less, and will ideally not exhibit significant reactivity with the cells of life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The "life-sustaining" tissues that are the most important from the standpoint of low reactivity, include heart, kidney, central and peripheral nervous system tissues and liver. The term "significant reactivity", as used herein, refers to an antibody or antibody fragment, which, when applied to the particular tissue under conditions suitable for immunohistochemistry or flow cytometry, will elicit either no staining or negligible staining with only a few positive cells scattered among a field of mostly negative cells.

However, as these aspects of invention are concerned with overcoming an aberrant signal or phenotype, antibodies directed against antigens that are not totally tumor-specific will likely still be useful for therapy as they will not adversely effect normal cellular function in a significant manner. If desired, the binding properties of a given antibody may be readily evaluated using conventional immunological screening methodology, as will be known to those of skill in the art in light of the present disclosure.

Tumor antigens contemplated for targeting in accordance with this invention include, for example, milk mucin core protein, human milk fat globule; TAG 72 or the HER-2 proto-oncogene protein, which are selectively found on the surfaces of many breast, lung and colorectal cancers; and the high $M_r$ melanoma antigens recognized by the antibody 9.2.27. High-selectivity antibodies contemplated to be particularly useful include, for example, B72.3, PR5C5 or PR4D2 for colorectal tumors; HMFG-2, TAG 72, SM-3, or anti-p $185^{Her2}$ for breast tumors; anti-p $185^{Her2}$ for lung tumors; 9.2.27 for melanomas; and MO v18 and OV-TL3 for ovarian tumors. In certain tumors, it is contemplated that alterations in the expression of key genes other than c-fos may be equally or even more important for inducing cell cycle arrest, depending on the cell-surface molecule that initiates the signal.

Naturally, in the practice of the invention, one will prefer to ensure in advance that tumors to be targeted clinically express the antigen ultimately selected. Techniques to verify this will be known to those of skill in the art, and involve antigenically testing a tumor tissue sample, for example, a surgical biopsy, or testing for circulating shed antigen. This can readily be carried out in an immunological screening assay such as an ELISA, wherein the binding affinity of antibodies from a "bank" of hybridomas are tested for reactivity against the tumor. Antibodies demonstrating appropriate tumor selectivity and affinity may then selected for use in the present invention.

As used herein, the term "antibody" is intended to refer broadly to any immunologic binding agent such as IgG, IgM, IgA, IgE, F(ab')$_2$; single domain or univalent fragments such as Fab', Fab, Dab; as well as engineered antibodies such as recombinant antibodies, humanized antibodies, bispecific antibodies, and the like. In preferred embodiments, it is contemplated that one will, at least initially, wish to employ a bispecific antibody as this will facilitate receptor cross-linking. In certain embodiments, the use of monoclonal antibodies is contemplated, such as those derived from rabbit, human, murine, monkey, rat, hamster, rabbit or chicken sources. The ultimate use of human or 'humanized' chimeric antibodies is also contemplated. Such 'humanized' constructs may be obtained from mouse, rat, or other species, and generally bear human constant and/or variable region domains.

In treating B cell tumors, it is contemplated that advantages may be found in employing an antibody which displays an increased affinity for the $F_c$ receptor, in that occupation of the $F_c$ receptor may potentiate the negative signal from sIg antibody binding.

Also intended to be included within tumor cell cycle arrest-inducing compositions are the natural ligands of various cell surface receptors, such as the biological ligand(s) for CD19. This is the agonist, rather than antibody, approach. It is envisioned that natural agonists, or synthetic molecules with similar structures, or even natural or synthetic antagonists, would be useful in effecting tumor cell cycle arrest. They may be employed alone, or in combination with an antibody against the specific receptor, other receptors, or with other therapeutics.

The compositions for use in inducing tumor cell cycle arrest may further comprise pharmaceutical agents other than antibodies or agonists that are capable of inducing or maintaining cell cycle arrest. Such components are contemplated to include, for example, cytokines such as $\gamma$ IFN and TGF-$\beta$; compounds which induce terminal differentiation, including polar/apolar compounds such as hexamethylene bisacetamide, and also retinoic acid; and agents which interfere with signal-transduction in a specific tissue.

Novel compounds, or candidate substances, capable of inducing tumor cell cycle arrest may be identified by employing further methods of the present invention. To identify a candidate substance capable of inducing cell cycle arrest in tumor cells, one would first contact a population of tumor cells with the candidate substance for a period of time sufficient to allow arrest to be induced. One would then analyze the population of tumor cells for the presence of cells which may be characterized as being under cell cycle arrest according to the criteria of the present invention, such as for example, as being in cell cycle stage $G_0/G_1$, as being small, as having inactive nuclear morphology, or as having increased levels of AP1 transcription factors, such as c-fos or c-jun.

It is also contemplated that cell cycle arrest of tumor cells may ultimately be achieved by bypassing the signal transduction pathways, and altering gene expression directly. For example, it is envisioned that the levels of protooncogenes or transcriptional activators, such as c-fos, may be increased artificially, such as by supplying DNA constructs encoding the specific gene to tumor cells. Techniques directed to such gene therapy will be generally known to those of skill in the art.

In still further embodiments, the present invention concerns other distinct methods of inhibiting tumor cell growth or reproduction, as may be used to effect more complete cancer therapy. To inhibit tumor growth, reproduction or progression, including metastasis, in accordance with this aspect of the invention, one would first employ the methods described above to identify a population of tumor cells which includes tumor cells in cell cycle arrest. One would then contact the tumor population with a composition capable of killing tumor cells under cell cycle arrest. In the treatment of animals with cancer, including human subjects, this may be achieved by administering such a composition, in a pharmacologically acceptable vehicle, to the patient.

This approach is contemplated to be particularly suitable for the more complete treatment of animals, including human subjects, with various types of cancer. The occurrence of tumor cells under cell cycle arrest within human malignancies will generally impede the chemotherapeutic destruction of the tumor, as conventional agents act preferentially on cycling cells, and are relatively ineffective at killing resting cells. The present invention, which allows the identification of arrested cells, will thus reduce the likelihood of any tumor cell escaping destruction, and will enable cancer patients to make more complete recoveries.

Compositions contemplated to be of use in killing tumor cells under cell cycle arrest include those agents that damage DNA; alkylating agents, such as methotrexate, doxorubicin, cis-platinum, cyclophosphamide, vincristine, bleomycin and prednisone; or immunotoxins (ITs). Immunotoxins are considered to be particularly useful agents for killing cell cycle arrested tumor cells in that they are known to be capable of killing resting cells, including resting B and T lymphocytes, and that they are more effective against resting than activated, replicating T cells. In addition, since immunotoxins inactivate ribosomes and thereby stop protein synthesis, it is unlikely that they would be mutagenic like most other chemotherapeutic agents.

The most useful immunotoxins for use in accordance with the present invention are contemplated to be those in which the antibody component is directed against the same battery of cell surface tumor markers outlined above and listed in Table I. In the treatment of B cell tumors, the use of anti-CD22 and anti-CD19 ITs, and preferably, a combination of both, is preferred. ITs targeted against the milk mucin core protein may be employed to combat breast tumors, and in general, the use of ITs directed against any tumor antigen, such as those in Table I, is contemplated. ITs will preferably include monoclonal antibodies linked by a heterobifunctional cross linker, such as SMPT, to any one of a variety of toxic agents, for example, deglycosylated ricin A-chain. The preparation and use of immunotoxins is generally known to those of skill in the art, for example, see U.S. Pat. No. 4,797,359, incorporated herein by reference.

Of course, the methods of the present invention directed to killing cell cycle arrested tumor cells may be advantageously combined with a variety of other strategies generally used in cancer treatment. For example, immunotoxin compositions, such as anti-CD22 or anti-CD19 ITs may be administered in combination with agents such as, for example, cyclophosphamide, doxorubicin vincristine, bleomycin, prednisone or methotrexate.

BRIEF DESCRIPTION OF THE DRAWINGS

The file of this patent contains at least one drawing executed in color. Copies of the color drawing(s) will be provided by the Patent and Trademark Office upon request and payment of the necessary fee FIG. 1. Flow cytometric identification of CCALC. Splenocytes from Id-immune control mice, Id-immune mice with CCALC, and non-immunized mice bearing clinically progressing $BCL_1$ tumor were analyzed for their light scatter profile (left column), and their expression of Thy1 vs. $\lambda$ (middle column), and $\kappa$ vs. $\lambda$ (right column). 10,000 events, gated to exclude non-viable cells, are shown for each plot. In the left and middle columns, the $\lambda^+$/Thy1$^-$ population is colored red with the remaining cells gray. In the right column, the $\lambda^+$ population is colored light blue or violet, delineating the $\kappa^+$ or $\kappa^-$ subset, respectively. Flow cytometry was performed on a FACScan equipped with an argon ion laser tuned at 488 nm. Forward light scattering, orthogonal light scattering, FITC and PE signals were determined for 30,000 cells. Data was displayed with "paint-agate" software.

DETAILED DESCRIPTION OF THE PREFERRED EMBODIMENTS

Figure 1:
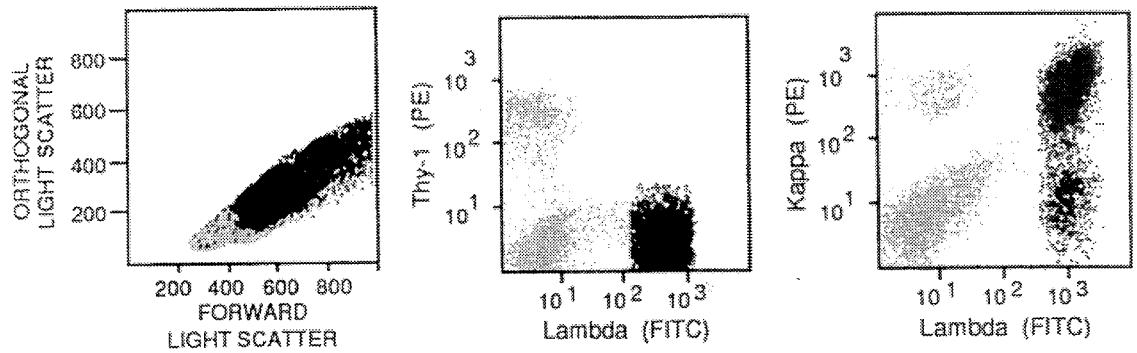
Figure 1:
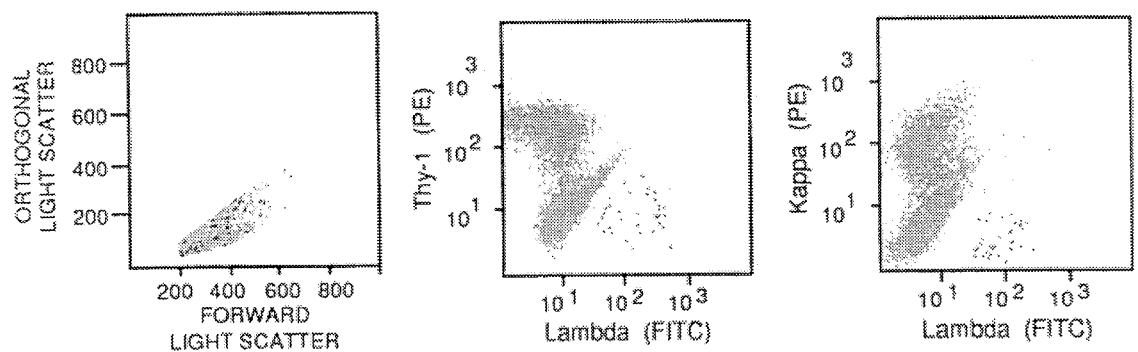
Figure 1:
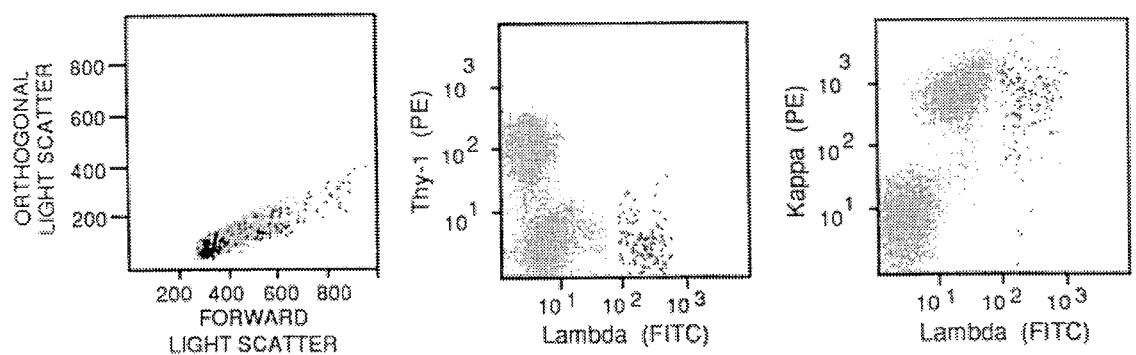

The term tumor dormancy is used to describe the situation wherein tumor cells have entered a prolonged quiescent state in which tumor growth is not clinically apparent. This is a resting stage from which the tumor can re-emerge at a later date, as may be evidenced by subsequent tumor growth, or by the transfer of tumor cells which initiate tumor growth in another animal.

Despite the importance of the dormancy phenomenon to clinical and basic science, there remains relatively little documented information on the mechanisms that underlie the induction, maintenance, and loss of tumor dormancy. In particular, it is important to note that prior to the present invention the term 'dormant' was employed generally to a wide variety of cases, and conveyed little if any information as to the molecular status of such cells. In fact, the term tumor dormancy has been erroneously employed to refer to premalignant states.

It is currently thought that the initiation of dormancy is predominantly a cytotoxic T-cell mediated process, and that the maintenance of this state is also a cell-mediated event, which additionally involves activated macrophages. With respect to the treatment of human B cell lymphoma with anti-idiotype, it has been reported that the extent of T cell infiltration before therapy correlates with the efficacy of anti-Id treatment, suggesting that cellular immunity to the tumor presumably is conducive to a favorable response.

BCL$_1$, a tumor that arose spontaneously in an elderly BALB/c mouse, was the first B cell lymphoma described in that species (Slavin et al., 1978). The clinical characteristics of BCL$_1$ resemble the prolymphocytic form of chronic lymphocytic leukemia in humans. BCL$_1$ cells bear surface immunoglobulin of both the μ/$\lambda$ and $\delta$/$\lambda$ isotypes that share a common idiotype (Id), as defined serologically and by sequence analysis (Krolick et al., 1979). In early studies, the inventors treated mice with advanced BCL$_1$ tumors with immunotoxins directed at the Ig Id, and observed that spleen cells from a proportion of animals that went into long-term remissions were still able to adoptively transfer BCL$_1$ tumors to syngeneic recipients (Krolick et al., 1982). Since tumor cells remained viable in the absence of clinical evidence of tumor growth, it was postulated that an anti-Id response was inducing a dormant state in the tumor cells.

The inventors reasoned the BCL$_1$ tumor to be a good model for the study of tumors as it has the following advantages: 1) the immunoglobulin idiotype (Id) is a clonal marker and therefore represents a tumor-specific antigen. The inventors thus proposed that anti-Id antibodies may be used to identify and isolate tumor cells. 2) DNA V$_H$ region gene rearrangements also represent a clonal marker which should facilitate detection of minimal disease by polymerase chain reaction (PCR). 3) The $BCL_1$-Ig contains a rare λ-chain-type, $λ_3$ which operationally is equivalent to a tumor-specific marker. 4) The tumor grows primarily in the spleen and can be precisely quantified by both Id analysis and transfer of graded numbers of splenocytes from tumor-bearing animals to syngeneic recipient animals. Adoptive transfer of tumor is an important advantage, particularly as a single $BCL_1$ cell can transfer tumor to a naive animal. 5) Splenic enlargement (the term splenomegaly will be used for simplicity) can be detected by palpation (single blind) and the results correlate closely with the content of $Id^+$ cells in the spleen. This simple noninvasive maneuver thereby allows for repeated observations on an individual animal. 6) $BCL_1$-bearing mice are markedly immunosuppressed like patients with B-cell lymphoma.

In the present study, the $BCL_1$ tumor model was employed as a means to analyze in detail the cellular and molecular mechanisms underlying changes in malignant phenotypes. In particular, this model was employed to isolate dormant lymphoma cells for further analysis. High resolution, multiparameter flow cytometry was employed to identify and subsequently isolate (by fluorescent-activated cell sorting, FACS) dormant cells in the spleen. The technique is based on the assumption that, given appropriate markers, dormant cells will have a unique "signature" of physical and antigenic characteristics (qualitative and quantitative) that allow separation from normal splenocyte populations.

A cytometry software program—PAINT-A-GATE—was utilized that allows the simultaneous analysis of cell surface density of 4 MAb-defined antigens and two scatter parameters (forward and orthogonal, which give information on cell size and complexity, respectively). This simultaneous analysis enables a search for unique clusters of cells in six-dimensional space that is consistent with a dormant tumor cell population, i.e., a population that expresses appropriate antigens and is present only in animals with dormant tumor. The inventors reasoned that using this technique, with a defined combination of MAbs, would lead to the identification of a unique cluster of cells which, when sorted, would be the only cells in the spleen capable of producing a $BCL_1$ tumor in naive recipients.

In such studies it was determined that dormancy was induced in 70% of 320 BALB/c mice immunized with $BCL_1$ immunoglobulin and subsequently challenged with $10^6$ $BCL_1$ cells. 95% of such mice were shown to contain $BCL_1$ cells by either cell transfer, or, eventual loss of dormancy. Employing the multi-parameter FACS method, dormant and malignant tumor cells were isolated from appropriate animals. Since the animals immunized with $BCL_1$Ig had developed a strong anti-Id response, the Id on the dormant cell surface was coated with host-derived Ig, and was therefore not useful for FACS isolation. However, $BCL_1$ Ig contains the l3 light chain, which is extremely rare in normal B lymphocytes, and this marker served as the basis for cell isolation by FACS.

Only animals harboring dormant tumor cells were found to contain lymphocytes double positive for both κ and λ staining, λ derived from the $BCL_1$Ig and kappa derived from the host-expressed anti-Id bound to the cells from the outside. In normal mice k and l double positive B lymphocytes are virtually nonexistent due to allelic exclusion at the light chain locus.

Staining of sorted dormant cells with the DNA dye, Hoechst, showed a 95% decrease in the number of $BCL_1$ in $S_1G_2M$ compared to growing $BCL_1$. Therefore, and of prime importance, the vast majority of dormant cells are in cell cycle arrest. Dormant cells will thus subsequently be referred to as under cell cycle arrest or more particularly, as being cell cycle-arrested lymphoma cells (CCALC). Cell cycle analysis indicates that the small CCALC are not dividing and that the small percentage of CCALC in $S_2G_2$ or M are in the larger cell compartment. This data suggests that the small cells have been induced to leave cell cycle because of the ligand-cell interaction(s) and that the large cells are partially but not completely arrested in cell cycle.

Morphological analyses showed $BCL_1$ tumor cells to be large, malignant appearing lymphoid cells with abundant cytoplasm, large nuclei, multiple prominent nucleoli, and open reticular chromatin. In contrast, the majority of CCALC were small and their nuclei had clumped chromatin and absent or inconspicuous nucleoli. Many of the CCALC have a plasmacytoid appearance. A minority of CCALC were medium-sized with larger, more actively appearing nuclei, but these did not approach the malignant appearance of the typical $BCL_1$ tumor cell. These findings are consistent with the results of cell cycle analysis, i.e., CCALC have entered a resting state or a state of terminal differentiation or both.

As mentioned above, prior to the studies presented herein, there was no data which related in vitro observations on the cell cycle of normal or neoplastic cells to the more complex situations encountered in vivo. Neither was it known whether dormant cancer cells continued to divide and were killed at the same rate, or whether cell division did not occur. Therefore, the importance of the unique aspects of the present invention, namely in characterizing dormant tumor cells at the molecular level, in defining them as under cell cycle arrest, and in studying cell cycle arrest mechanisms in vivo, cannot be overstated.

Analysis of various oncogenes that have been implicated in signalling $BCL_1$ cells indicates that only one appears to be unexpectedly altered in expression in CCALC. This being c-fos, which is elevated approximately 10-fold in CCALC compared to both growing $BCL_1$ and normal small B cells. This suggests that c-fos plays a critical role in induction of dormancy, and that the expression of this early activation gene has been uncoupled from entry into the cell cycle. The engagement of Ig on the cell surface of $BCL_1$ cells is proposed to activate a signal transduction pathway leading both to the induction of dormancy and an upregulation in c-fos mRNA levels. Furthermore, since the Fos protein is a component of the AP1 group of transcription factors, this suggests that the induction of cell cycle arrest in tumor cells is an active process, and that it may be inducible by other AP1-like transcription factors.

When resting cells are stimulated to proliferate in culture by the addition of serum or growth factors, the transcription of a set of genes termed immediate early-response genes is induced. Included in this set are the proto-oncogenes c-myc, c-fos and c-jun, suggesting that these genes must play a central role in the control of cell growth. In the case of c-fos, steady-state mRNA levels increase rapidly, peaking within 10 minutes after stimulation, and then returning to pre-stimulation levels by 60 minutes. The kinetics of c-myc induction are slightly delayed as compared with c-fos, and the amount of c-myc mRNA returns to a level intermediate between the induction peak and the amount present in resting cells. Thus, in most model systems c-myc levels are higher in proliferating cells than in resting cells, while c-fos levels are low in both. The finding that c-fos levels are high in the CCALC indicates that in this system c-fos expression has been uncoupled from cell cycle progression.

Several genes have been isolated which show sequence similarity to either c-fos or c-jus, including fosB and fra-1 (fos-related antigen-1), and junB and junD. Both Fos and Jun family members contain leucine zipper dimerization domains. Fos/Jun heterodimer and Jun/Jun homodimer complexes are found in purification fractions that have been termed AP-1. These complexes are able to function as transcription activators through the interaction with specific DNA sequences (TGACTCA) found in a variety of viral and cellular promoters. Although distinction between the different complexes in terms of DNA-binding affinity, specificity, or transcription activation have yet to be found, one striking difference between Jun/Jun and Fos/Jun complexes has been observed—they bend DNA in different ways. Differential bending of promoter elements may provide to be one of the mechanisms that provide for differential regulation of gene expression by these two distinct complexes.

Since dramatic differences in the levels of c-fos and c-jun mRNA have been observed in cell cycle arrested tumor cells, one may expect the level of AP-1 binding activity to also be different. Binding activity may be examined using mobility shift assays with synthetic AP-1 sites as binding probes. As both c-fos and c-jun levels are greatly increased in cell cycle arrested tumor cells, a large increase in the level of AP-1 binding activity in these nuclear extracts may be observed. Alternatively, since these proteins bind to DNA as homo- and heterodimers between themselves and other Jun family members, the overall effect of c-fos and c-jun induction might be to change the quality rather than the quantity of AP-1 binding complexes.

The pattern of binding complexes in a mobility shift assay with an AP-1 site probe can be expected to be quite complicated in light of the possible combinatorial interactions of Fos and Jun family members. Indeed, using crude nuclear extracts the inventors have observed several AP-1 binding complexes from crude nuclear extracts. In order to elucidate the identities of the proteins involved in such complexes, the inventors contemplate using family- and protein-specific antisera raised against the c-fos or c-jun proteins in combination with mobility shift assays. These assays include standard mobility shift assays using AP-1 site probes and crude nuclear extracts, and "supershift" assays employing protein-DNA complexes and specific antisera.

The most straightforward interpretation of the results to date is that c-fos and/or c-jun induction results in an increase in AP-1 site binding activity, which increases the transcription of genes containing AP-1 promoters, which, in turn, results in cell cycle arrest. If this model is true, fit-1 will likely also be induced in arrested tumor cells. Alternatively, if a direct cell cycle arrest pathway involving c-fos and/or c-jun is not readily apparent, this does not negate the important correlation between their elevated levels and cell cycle arrest. Regardless of the ultimate mechanism, the present invention demonstrates that increases in the levels of these species of mRNA are clearly indicative of cell cycle arrest, and are thus useful in determining optimal therapeutic approaches.

Studies are contemplated to determine whether fos expression is sufficient to induce dormancy. The model described above, in which cell surface signals are transduced into the nucleus leading to c-fos induction and the transactivation of a set of genes necessary to illicit cell cycle arrest, suggests the Fos protein to be the master regulator of dormancy. If this proves to be the case, the inventors contemplate that the original signal transduction pathway may be bypassed and that cell cycle arrest may be induced by activating c-fos expression artificially. To examine this possibility, the inventors propose to prepare DNA constructs in which Fos activity can be artificially induced, to introduced such constructs into cells, such as $BCL_1$ cells, to determine their effects on malignant growth and cell cycle arrest in vivo and in vitro.

Ultimately, it is contemplated that tumor cell cycle arrest may be induced by gene therapy. DNA encoding key genes in this process, such as, for example, c-fos or c-jun, may be applied directly to cells, in the form of oligonucleotides, or other genetic constructs. It has been shown that oligonucleotides can successfully traverse cellular membranes. Other techniques for direct insertion in the cells include, by way of example, electroporation, or calcium phosphate transfection.

The preparation of vectors which incorporate nucleic acid sequences capable of encoding the desired genes, once introduced into the cells to be treated, is also contemplated. In this regard, replication defective retrovirus, such as LNSX, LN or N2A, may be used, as may other vectors such as adenovirus or vaccinia viruses. Oligonucleotides or DNA vectors could be packaged prior to administration to ensure stability their in circulation, for example, by liposome encapsulation.

Since a prediction of the model is that expression of c-fos will lead to growth arrest it will be necessary to use expression systems in which fos activity can be regulated. Unfortunately, this is not readily achieved in eukaryotic systems. The main problems with most of the off-on transcriptional systems used are that 'off' is not really off, and that on is relatively weak. Therefore the inventors contemplate using the a system specifically developed for the strong induction of Fos activity. A chimeric gene has been constructed in which the Fos protein becomes covalently linked to the hormone-binding domain of the estrogen receptor (ER). In the absence of hormone this domain has the interesting ability to suppress transactivation of transcription factors. If hormone is added, the suppressing activity of the domain is inactivated and transactivation can proceed. Transcription and translation of this chimeric Fos-ER gene can be constitutively on and transactivation regulated by hormone. The Fos-ER chimeric gene may be expressed from the SV40 promoter/enhancer.

Several studies are contemplated to assay the effects of fos expression, and a variety of other protooncogenes, on malignant growth and cell cycle arrest, both in in vivo and in vitro. The most essential study will be to examine the effects of Fos-ER activation by hormone on malignant growth and dormancy induction in vivo. Transfected clones will be introduced into normal Balb/c and Id-immune mice, in controlled experiments, and malignant growth be evaluated by non-invasive splenic palpation. Fos-ER clones and controls will be introduced into both types of recipients in the presence and absence of β-estradiol, and the kinetics and magnitude of malignant growth determined.

If splenomegaly is not detected in a group of the experimental mice it will be important to demonstrate the presence of cell cycle arrested tumor cells. Spleen from mice >60 days after tumor cell transplant will be analyzed for arrested $BCL_1$ cells by FACS, employing the methods of the present invention. In addition, arrested cells isolated from these mice will be introduced into secondary recipients to determine if they are tumorigenic in the absence of hormone. Naturally, the morphology of such cells will be examined to determine if hormone-induced Fos activation results in the same alterations as Id immunity. The mRNA levels of c-fos, c-jun, c-myc, and other oncogenes will also be determined using quantitative PCR.

It may be determined that Fos plays an important role in induction of dormancy induced by mIg crosslinking of $BCL_1$ cells, but that induction of Fos expression alone is not sufficient to induce cell cycle arrest. The inventors contemplate addressing this question by inducing cell cycle arrest under standard conditions, but repressing Fos expression. The use of antisense RNA to inhibit the translation of expressed mRNA will be employed to determine whether Fos expression is necessary to induce cell cycle arrest. $BCL_1$ cells expressing c-fos antisense will be introduced into Id-immune mice. If Fos induction is necessary for cell cycle arrest, all such mice should rapidly develop splenomegaly, since the c-fos induced by mIg crosslinking will be inactivated by c-fos antisense.

Regardless of what the roles of cellular protooncogenes are ultimately found to be, the importance of the present invention in allowing the characterization of arrested tumor cells will be readily acknowledged. It must be stressed that the cell cycle status, size, and morphological characterizations disclosed herein provide more than enough examples by which to identify the presence of dormant tumor cells within a malignant population, and thus allow the most appropriate clinical therapy to be designed. Accordingly, in the clinical treatment of tumors, one may wish to employ components that induce tumor cells to enter the $G_0/G_1$ cell cycle phase, or to maintain cells in this phase, and which result in the generation of small tumor cells or tumor cells with inactive nuclear morphology.

It is believed that the results presented herein, and further studies employing the $BCL_1$ tumor model, will facilitate the elucidation of the cellular mechanisms which lead to cell cycle arrest. The SCID antibody model will be especially useful for separating the contributions of antibody, cellular immunity and nonspecific effector mechanisms in the induction of dormancy. Due to the absence of a host-immune response, the SCID model also allows human tumors to be analyzed and heterologous anti-receptor antibodies or other receptor-ligands to be administered for extended periods of time.

The findings from the present study have two particularly important implications for the clinical treatment of cancer. Firstly, malignancies which are not amenable to standard therapeutic protocols, might be approached from the standpoint of dormancy induction rather than tumor destruction. It is envisioned that long-term remissions may be induced in a variety of aggressive malignancies by the identification and use of agents capable of inducing and/or maintaining tumor cells in a state of cell cycle arrest. These agents would likely alter cell signalling pathways, particularly those which increase the levels of AP1 transcription factors and consequently activate AP1 responsive genes. An example of the increase in expression of key regulatory genes, is the activation of the cellular protooncogene c-fos, and even c-jun.

Suitable cell cycle arrest-inducing agents are contemplated to include antibodies directed against molecules present at the surface of tumor cells, including surface tumor markers such as sIg, or the $F_c$ receptor, or CD19-like molecules. For example, if the human immune response to a tumor is too weak to induce dormancy, it is envisioned that the patient may be actively or passively provided with the required immunity by administering one or more suitable agents, such as antibodies. Such therapeutic intervention could be employed to diminish cycling dormant cells after the removal of a primary tumor, and thus to significantly delay the emergence of escapees.

Further agents which are envisioned to be useful as therapeutics in this regard include cytokines such as $\gamma$ IFN and TGF-$\beta$, hexamethylene bisacetamide, and retinoic acid.

Also contemplated, are the use of antigen-specific solubilized T cell receptors or antibodies that imitate the specificity of T cell receptors, as well as the natural ligands of cell surface receptors, such as CD19, their synthetic counterparts, or even natural or synthetic antagonists.

The second important treatment aspect resulting from the present invention concerns the fact that the occurrence of tumor cells under cell cycle arrest within human malignancies may impede the chemotherapeutic destruction of the tumor. This is because conventional chemotherapeutic agents preferentially act on cycling cells (Clarkson et al., 1977) and are relatively ineffective at killing resting cells, such as CCALC. The only group of agents that appear to act independent of the cell cycle are the alkylating agents that can damage DNA in nondividing cells. However, if the nondividing cells have sufficient time to repair the damaged DNA before cell division, then even these agents might be ineffective.

As the present invention allows, for the first time, arrested tumor cells to be unequivocally identified, this will permit alternative therapeutic strategies to be designed and utilized. Treatment protocols designed specifically for the treatment of cancers in which arrested cells have been identified may include, for example, the use of pharmaceutical agents such as immunotoxins that can kill resting cells (Vitetta et al., 1983). Preliminary evidence has shown that resting B and T cells are readily killed by cell specific-immunotoxins.

Techniques for preparing monoclonal antibodies against antigenic cell surface markers will be known to those of skill in the art, as exemplified by the technique of Kohler & Milstein (1975). Generally speaking, the preparation of monoclonal antibodies against tumor antigens involves repeated injection of the antigen composition into mice, the harvest of spleen cells and their fusion with myeloma cells, such as SP2/0 cells, by standard protocols (Kohler & Milstein, 1975). Hybridomas producing antibodies with the appropriate reactivity may be cloned by limiting dilution, and the most suitable antibody-producing hybridomas identified by screening using, e.g., an ELISA, RIA, IRMA, IIF, or similar immunoassay.

Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. Although early immunotoxins suffered from a variety of drawbacks, more recently, stable, long-lived immunotoxins have been developed for the treatment of a variety of malignant diseases. These "second generation" immunotoxins employ deglycosylated ricin A chain to prevent entrapment of the immunotoxin by the liver and hepatotoxicity. They employ new crosslinkers which endow the immunotoxins with high in vivo stability and they employ antibodies which have been selected using a rapid indirect screening assay for their ability to form highly potent immunotoxins.

The use of toxin-antibody constructs is well known in the art of immunotoxins, as is their attachment to antibodies, for example, see U.S. Pat. No. 4,340,535, incorporated herein by reference. However, certain advantages may be achieved through the application of preferred technology, both in the preparation of the immunotoxins and in their purification for subsequent clinical administration. For example, the use of certain linkers, such as those with a sterically hindered disulfide bond, will generally be preferred due to their greater stability in vivo, thus preventing release of the toxin moiety prior to binding at the site of action. The most preferred cross-linking reagent is SMPT, although heterobifunctional photoreactive phenylazides may also be used.

A wide variety of cytotoxic agents are known that may be conjugated to immunotoxins, including plant-, fungus- and bacteria-derived toxins, such as various A chain toxins, particularly ricin A chain, ribosome inactivating proteins such as saporin or gelonin, α-sarcin, aspergillin, restrictocin, ribonucleases such as placental ribonuclease, angiogenin, diphtheria toxin, and pseudomonas exotoxin, to name just a few. A preferred toxin moiety is deglycosylated ricin A chain (dgA), and the use of truncated or recombinant A chain is also contemplated. Once conjugated, the immunotoxin may be purified to remove contaminants such as unconjugated A chain or binding agent, for example, by using Blue-Sepharose with a gel filtration or gel permeation step.

It is contemplated that the therapeutic compositions of the present invention, including those comprising immunotoxins or other agents, will be formulated into pharmaceutical compositions, and preferably compositions that may be administered parenterally. Suitable pharmaceutical compositions in accordance with the invention will generally comprise the therapeutic agent admixed with a pharmacologically acceptable diluent or excipient, such as a sterile aqueous solution. Such formulations may include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

ISOLATION OF CELL CYCLE-ARRESTED LYMPHOMA CELLS (CCALC)

1. Induction of Tumor Dormancy

It has been shown that the immunization of mice with murine myeloma Ig can induce specific immunity to the tumor presumably via an anti-Id response. Stevenson et al. (1990) have immunized BALB/c mice with $BCL_1$ Ig before challenge with $BCL_1$ and have induced dormancy in a proportion of such mice. Using the $BCL_1$ tumor model, the inventors have extended their findings and characterized this model biologically as a framework for elucidating the cellular and molecular mechanisms of cell cycle arrest. As will be discussed in more detail below, certain of the methods employed by the present inventors have shown, for the first time, that cell cycle arrest may be induced by antibodies alone.

A major goal was to utilize the above model to isolate and characterize dormant lymphoma cells. In non-immune mice injected with $10^6$ $BCL_1$ cells, the tumor grows rapidly, splenomegaly is detectable by palpation by 23–42 days after injection, with most animals succumbing to advanced tumors within 2 months. However, if the mice are immunized with $BCL_1$ Ig prior to injection of tumor cells (Uhr et al., 1991), 70% of mice survive beyond two months (mean of 140 days). Hence, 60 days was chosen as a designation of dormancy, i.e., spleens that had not enlarged by 60 days were considered to harbor dormant lymphoma cells.

To determine the degree of splenomegaly, the ventral surface of the mouse is divided into four quadrants progressing from the left rib cage to the right rib cage and each quadrant line is assigned a splenic index with values of 1, 2, 3, and 4 with the median line assigned the value of 2. The spleen of a normal 12-week-old BALB/c mouse has a value of 0.5; i.e., it extends halfway between the left rib cage and the first quadrant line given the value of 1. A spleen that extends to the median line is given a value of 2 and one that extends to the right rib cage a value of 4. Since infection or immunization can cause splenomegaly with a spleen index of 1.75, a spleen index of >2 was considered as indicative of tumor growth. Reproducibility of spleen palpation was demonstrated by the close correlation of repeated "blind" determinations of the same animals by a single individual and the number of $Id^+$ $BCL_1$ cells in the spleen. All determinations of splenomegaly were performed in a "blind" manner.

Tumor cells were determined to be present in approximately 95% of mice lacking enlarged spleens at 60 days, as demonstrated by transfer of tumor to syngeneic recipients, or regrowth of tumor at a later stage. However, $Id^+$ B cells were not detected by cell surface staining with anti-Id antibodies. Since the mice develop high titers of anti-Id antibody, the inventors postulated that endogenous anti-Id might be masking the cell surface Id on the tumor cells from subsequent analysis.

2. Isolation and FACS Analysis of CCALC

Following the findings described above, high resolution, multiparameter flow cytometry was employed to identify and subsequently isolate, by fluorescent-activated cell sorting (Terstappen et al., 1990), CCALC from the spleens of these animals. The use of FACS to isolate CCALC was based on the assumption that, given appropriate markers (other than Id), CCALC will have a unique "signature" of physical and antigenic characteristics (qualitative and quantitative) that will distinguish them from normal splenocytes, and allow their isolation. This was, indeed, found to be the case. Using combinations of monoclonal antibodies (MAbs) against λ-light chain, Thy1, Ia (class II MHC), and Mac-1 (CD11b) and the 2 scatter parameters, a unique cluster of cells from dormant spleens was identified; which cells were found to be the only cells capable of producing a $BCL_1$ tumor when transferred to naive recipients.

Flow cytometric analysis identifying CCALC in the spleen of an animal challenged with $BCL_1$ tumor cells following immunization with $BCL_1$ Ig is depicted in FIG. 1. In the animal immunized with the $BCL_1$ Ig without tumor challenge (Id-immune mouse), only 0.36% of splenocytes express the λ light chain (Thy1$^-$, λ$^+$; middle row, center panel). Essentially all of the λ$^+$ cells are κ$^-$ (middle row, right), reflecting isotype exclusion at the light chain loci. The λ$^+$ cells are both small and large as judged by scatter parameters (middle row, left), reflecting resting and activated states, respectively. In mice challenged with $BCL_1$ tumor cells in the absence of prior immunization ($BCL_1$ tumor), the tumor grows rapidly, and the spleen contains large numbers of Thy1$^-$, λ$^+$ tumor cells (top row, center). While these cells are not expressing endogenous κ, many of them appear to be double positive for κ and λ (top row, right). These double positive cells undoubtedly result from the binding of host derived κ-containing anti-$BCL_1$ antibody to the tumor cells. However, the tumor cell-antigen(s) (possibly the Id) appear to be in excess because a large number of $λ^+$ cells are not coated with Ig from the host. The $BCL_1$ tumor cells are all large (top row, left), reflecting their activated, malignant state.

If mice are immunized with purified $BCL_1$-Ig and then challenged with tumor cells, tumor dormancy is induced. Analysis of splenocytes from these animals reveals a relatively large increase in the number of $Thy1^-$, $λ^+$ cells (bottom row, middle; averaging 1.5±0.25% in 10 mice as compared with 0.24±0.09% in 7 normal Id-immune mice). These $λ^+$ cells are uniformly $Ia^+$, $Mac-1^-$ and over 90% are $κ^+$. This latter finding suggests that they are coated with endogenous anti-Id (bottom row, right) and supports the interpretation that few of these cells are normal $λ^+$ B cells. Most of these putative CCALC have the scatter profile of small lymphocytes, reflecting an inactive state (bottom row, left). Thus, in clinically stable Id-immune mice challenged with malignant $BCL_1$ cells 60 or more days prior to analysis, $1-2×10^6$ quiescent tumor cells are present in the spleen, and can be readily identified using the parameters described above.

3. Adoptive Transfer of CCALC

To confirm that the ($Thy1^-$, $Ia^+$) $λ^+$ population delineated by flow cytometric analysis are CCALC, the tumorigenic potential of these cells was examined in adoptive transfer experiments after their purification by FACS. ($Thy1^-$, $Ia^+$) $λ^-$ and ($Thy1^-$, $Ia^+$) $λ^+$ cells were sorted from a mouse harboring CCALC and compared with control, unseparated splenocytes from the same mouse and sorted ($Thy1^-$, $Ia^+$) $λ^+$ $BCL_1$ tumor cells (from an unimmunized mouse with progressive malignant splenomegaly) for their ability to transfer tumors in syngeneic recipients. As expected, transfer of tumors was readily accomplished with sorted, actively growing $BCL_1$ tumor cells (Table II). Splenocytes from mice harboring CCALC also transferred tumor, but only in a proportion of recipient mice. Significantly, there was an approximately 50-fold enrichment of cells capable of transferring tumors in the sorted $λ^+$ population as compared with total splenocytes, whereas sorted $λ^-$ cells were unable to transfer tumor (representative experiment of 3). These data not only confirm the identification of the CCALC in the spleen of these animals, but also indicate that a state of dormancy is reversible following transfer of CCALC into nonimmunized animals.

TABLE II

Transfer of $BCL_1$ Disease from CCALC

| Status of Tumor in Donor | Sorted For | No. Cells Transferred into Recipients | No. Mice with Splenomegaly Total No. of Mice[a] |
|---|---|---|---|
| Control $BCL_1$ | —[b] | $10^4$ | 4/4 |
| Control $BCL_1$ | $λ^+$ | $10^4$ | 5/5 |
| Dormant | —[b] | $5 × 10^4$ | 2/5 |
| Dormant | $λ^+$ | $10^4$ | 5/5 |
| Dormant | $λ^+$ | $10^3$ | 2/5 |
| Dormant | $λ^-$, $Thy1^-$ | $10^4$ | 0/5 |

[a]Examined day 65 post-transfer.
[b]Cells were exposed to antibodies and passed through the FACS without sorting.

EXAMPLE II

FURTHER CHARACTERIZATION OF CELL CYCLE ARRESTED TUMOR CELLS

1. Cell Cycle Status of CCALC

Figure 2A:
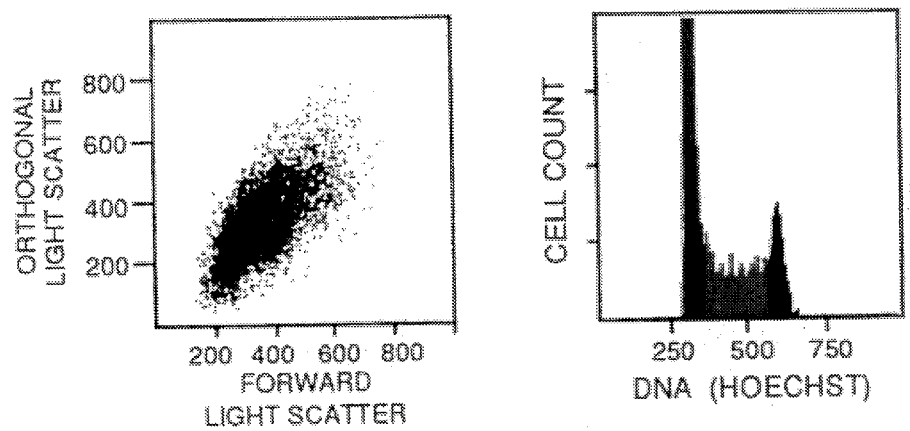
FIG. 2. A: Cell cycle analysis of CCALC vs. BCL$_1$ tumor cells. Splenocytes from Id-immune mice with CCALC, and non-immunized mice bearing clinically progressing BCL$_1$ tumor were simultaneously analyzed for their light scatter profile, DNA content (Hoechst 33342 staining), and expression of $\lambda$, Thy1, and Ia. 4300 events were collected gated on 1) the $\lambda^+$/Thy1$^-$/Ia$^+$ population, and 2) the width vs. area of the Hoechst 33342 signal (pulse analysis), so as to eliminate doublets and larger cell aggregates. The scatter and DNA profile of the gated cells are shown in the left and right columns, respectively. Cells in the G$_0$/G$_1$-phase of the cell cycle (1n DNA content) are colored violet, those in S-phase (between the 1 and 2n peaks) are colored light blue, and those in G2/M-phase (2n DNA) are colored black. B,C: Morphology of BCL$_1$ tumor cells (B) vs. CCALC (C). Splenocytes from Id-immune mice with CCALC, and non-immunized mice bearing growing BCL$_1$ tumor were stained for their expression of $\lambda$, Thy1 and Ia, and the $\lambda^+$/Thy1$^-$/Ia$^+$ populations were sorted, cytocentrifuged onto slides, fixed with methanol and stained with Wright/Geimsa. Growing BCL$_1$ cells (left panel; 750× magnification) have a large, immunoblast morphology with active-appearing nuclei (open chromatin and multiple, prominent nucleoli) and abundant gray cytoplasm. The great majority of CCALC (right panel; 750× magnification) are small to medium-sized and have eccentric, inactive nuclei (clumped chromatin with inconspicuous nucleoli) that gives the cells a plasmacytoid appearance. Occasional cells have a classical plasma cell morphology (open arrow). A minority of cells (closed arrow) are slightly larger with more active appearing nuclei, but are still clearly distinguishable from growing BCL$_1$ cells. The distribution of Hoechst staining intensity was displayed with "paint-a-gate" software. For multiparameter cell sorting, a dual-laser FACStar Plus was used and the fluorochromes FITC, PE, allophycocyanin and Texas red.
Figure 2A:
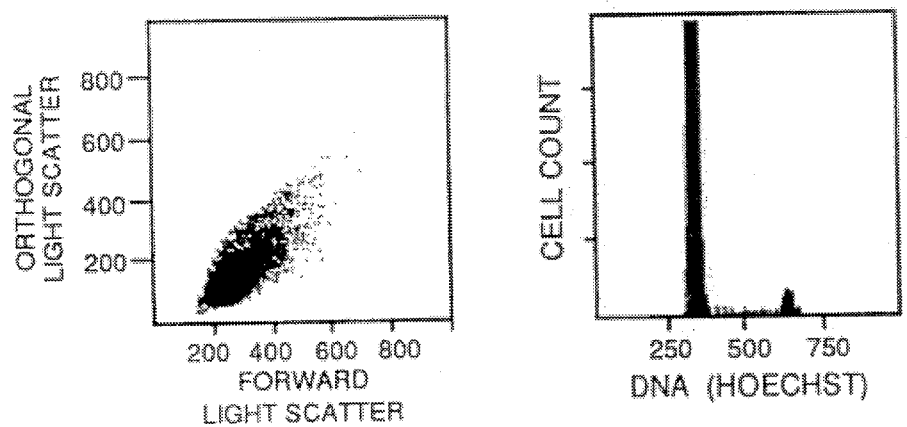

The cell cycle status of $BCL_1$ in dormant and tumor-bearing mice was determined using multiparameter flow cytometry. The $BCL_1$ cells were identified with anti-λ, Thy1 and Ia MAbs, and their DNA content determined by staining with the DNA-binding dye Hoechst 33342 (Kubbies et al., 1985). FIG. 2A depicts the scatter and dye-binding profiles of splenocytes gated as $λ^+$, $Ia^+$ and $Thy1^-$. In tumor-bearing mice, 17.6±5.9% of the growing $BCL_1$ cells are in the S (light blue) or $G_2$+M (black) compartments of the cell cycle. In contrast only 1.8±0.6% of the CCALC are in S+$G_2$+M. The CCALC are mostly smaller than the corresponding population of $G_0$+$G_1$ cells from the $BCL_1$ tumor (violet), suggesting that the vast majority of the CCALC are probably in $G_0$. The $BCL_1$ cells with a 1n DNA content are probably in $G_1$, prepared to initiate the next cycle.

Although there is a clear difference in the cell cycle status of growing and CCALC, there is a small proportion of CCALC which is cycling. These cycling cells might be expected to accumulate after several months of growth. However, since the number of CCALC does not increase for long periods of time, the low level growth of the CCALC must be balanced by cell death. Whether such death is an inherent property of the tumor cells or reflects the action of host mechanisms, immune or otherwise, remains to be determined.

An alternative method, the measurement of in vitro bromodeoxyuridine (BrdU) uptake by these cell populations using antibody specific to BrdU gave similar results to those above. These findings do not distinguish whether the large CCALC are cycling at a slow rate or a small percentage of the large cells are cycling at the rate of control $BCL_1$ (doubling time, about 3.2 days). Since the $BCL_1$ cells injected into Id-immune mice are all large cells, the small CCALC must be derived from the large $BCL_1$ cells. The origin of the larger CCALC is not clear. They could be derived from the rapidly cycling $BCL_1$ cells or all the CCALC may become small cells first and the larger cells may be derived from them. Thus, the larger CCALC may be the population of CCALC which is in a stage of escape. The population of small and larger CCALC may also be in a dynamic equilibrium.

2. Morphology of CCALC

Figure 2B:
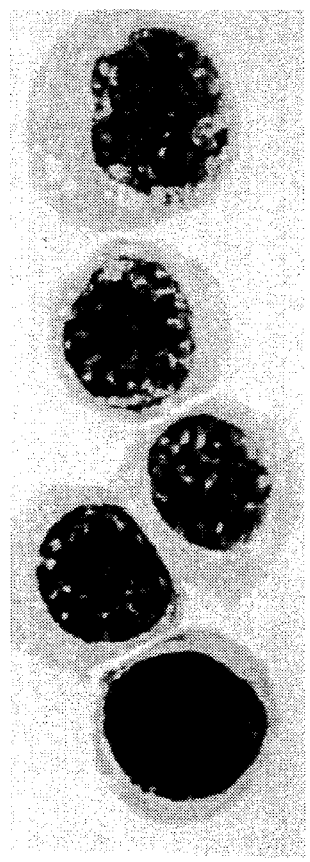
Figure 2C:
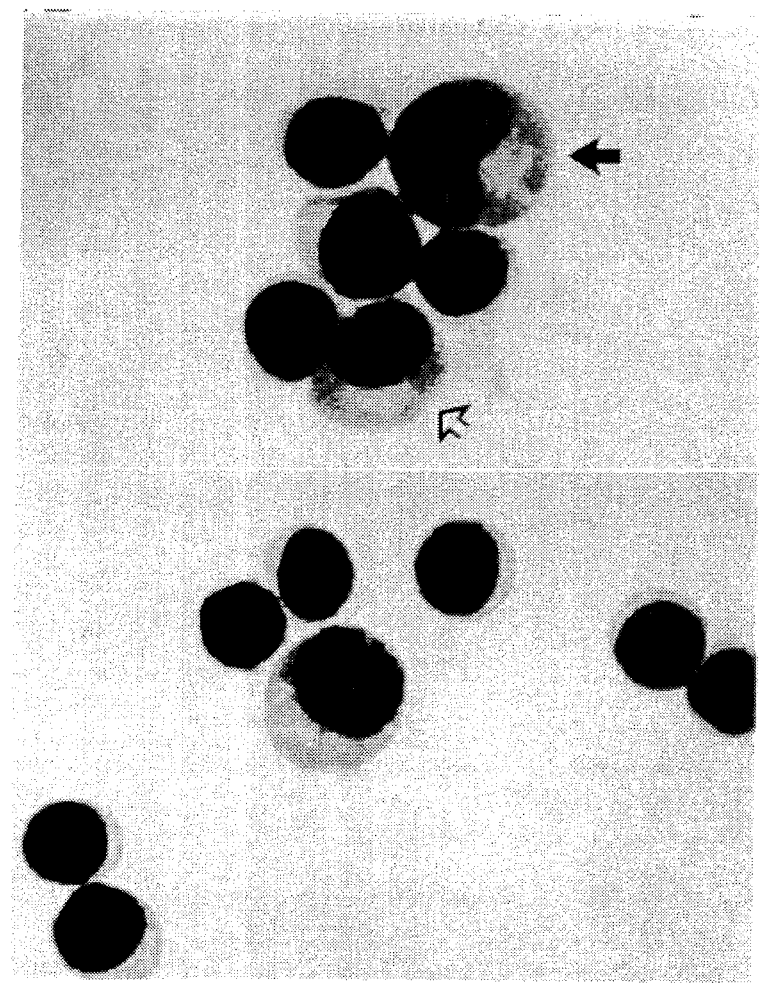

The difference in characteristics between growing $BCL_1$ and CCALC is also reflected in cellular morphology. $BCL_1$ tumor cells are large, malignant appearing lymphoid cells with abundant cytoplasm, large nuclei, multiple prominent nucleoli, and open reticular chromatin (FIG. 2B). In contrast, the majority of CCALC are small and display nuclei with clumped chromatin and absent or inconspicuous nucleoli (FIG. 2C). Many of the CCALC have a plasmacytoid appearance. A minority of CCALC are medium-sized and exhibit larger, more actively appearing nuclei, but even these do not approach the malignant appearance of the typical $BCL_1$ tumor cell. These findings are consistent with the results of cell cycle analysis, i.e., CCALC have entered a resting state or a state of terminal differentiation or both.

3. Immunophenotype of CCALC

Quantitative flow cytometry of control $BCL_1$, CCALC and normal B cells was performed. Expression of B-220 and MEL-14 molecules were increased 5 and 1.5-fold respectively on CCALC, whereas expression of PgP-1 was decreased by 50%. There were no marked differences in expression of Class II MHC antigens (I-A and I-E) and J11D, a marker for memory B cells. The relevance of these changes in expression of adhesion/activation molecules to induction of dormancy remains to be determined.

4. Expression of Oncogenes in CCALC

In order to begin to define the difference between CCALC and control $BCL_1$ at the molecular level, the expression levels of a panel of oncogenes that may be associated with cell cycle regulation were analyzed. A PCR-based quantification was employed which uses an internal standard to allow the absolute quantification of mRNA levels in terms of molecules/cell (Scheuermann et al., 1992). It should be emphasized that for each cell population the PCR reactions use the same cDNA preparation as template; the expression of specific genes is determined with the use of different amplification primer pairs. In the following studies, all three cell populations were found to express comparable levels of β-actin mRNA (bottom panel; 1700 molecules/cell for $BCL_1$ and normal lymphocytes, and 1400 molecules/cell for CCALC).

Figure 3A:
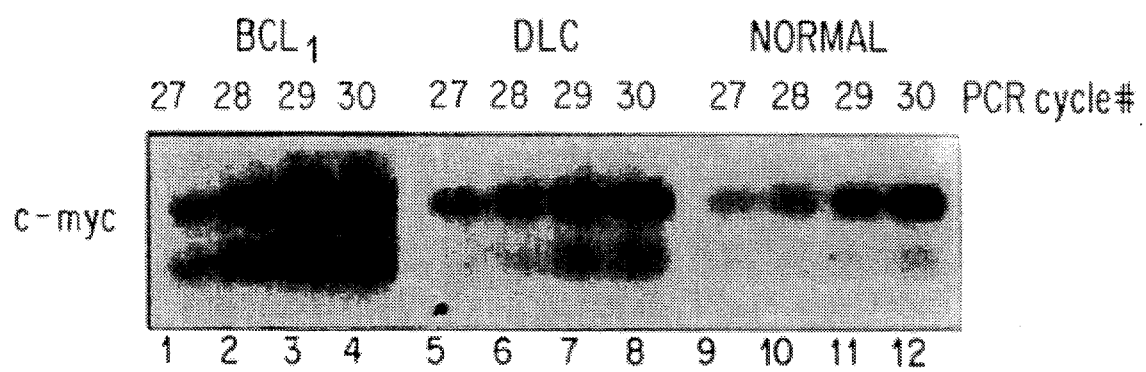
FIG. 3. Early activation oncogene expression in BCL$_1$ and CCALCs. mRNA levels of c-myc, c-fos and $\beta$-actin were quantified by PCR using an internal RNA standard (Scheuermann et al., 1992). Cells were isolated from the spleens by FACS as Thy1$^-$ and $\lambda^+$ for growing BCL$_1$ and CCALC, and Thy1$^-$ and $\lambda^-$ for normal B lymphocytes (as described in FIG. 2). cDNA was synthesized from a mixture of 10$^4$ cell-equivalents of total RNA and 10$^6$ (myc and fos panels) or 10$^7$ (actin panel) OQ-1 synthetic RNA molecules by random priming. PCR products derived from endogenous mRNA (e) and from the standard RNA (s) differ in size and can be distinguished following gel electrophoresis. A: Phosphorimage of cDNA-derived PCR products using $^{32}$P-labelled primer pairs for c-myc (top panel), c-fos (middle panel) and $\beta$-actin (bottom panel) following gel electrophoresis. cDNA derived from 250 cells of growing BCL$_1$ (lanes 1–4), CCALC (lanes 5–8) or normal B lymphocytes (lanes 9–12) was amplified for the indicated number of PCR cycles. B: Quantification of mRNA levels. Data from panel A was analyzed by phosphorimaging and plotted as e/s Vs. cycle number for BCL$_1$ (circles), CCALC's (squares) and normal lymphocytes (triangles).
Figure 3B:
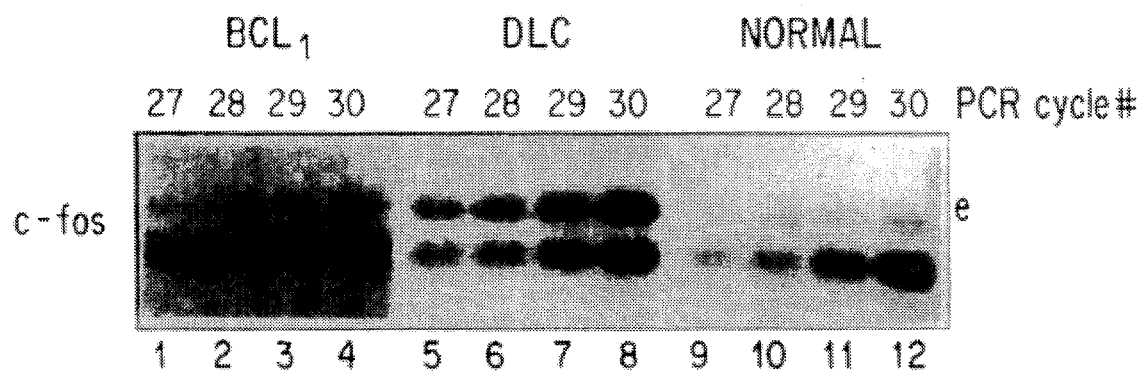
Figure 3C:
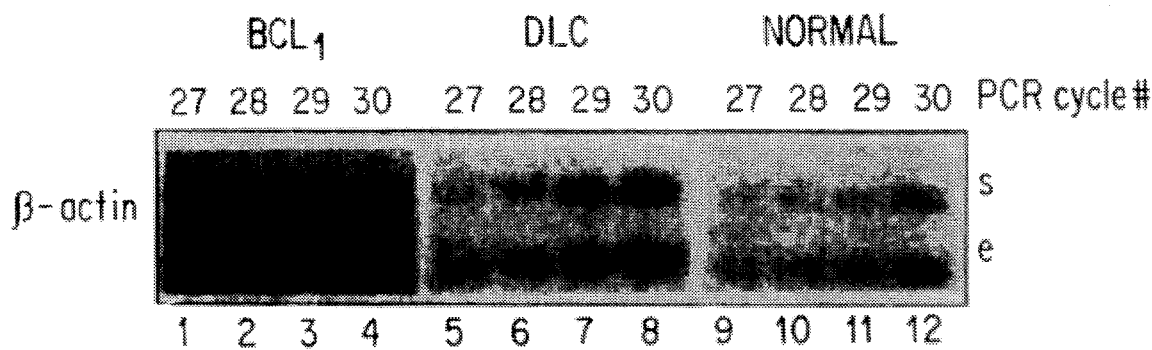

From the panel of oncogenes analyzed to date, no significant differences in the levels of lyn, blk, c-myb, bcl2 or p53 transcripts were detected between the dormant and malignant cell populations. The levels of c-fos and c-myc mRNA were thought to be particularly interesting as these genes have been implicated in the transition from $G_0$ to $G_1$. FIG. 3 shows the mRNA-derived PCR products generated from tumorigenic BCL1, CCALC and normal B lymphocytes. The amount of product generated from the endogenous c-myc mRNA (top panel) is great for rapidly dividing, tumorigenic $BCL_1$ (98 mRNA molecules/cell), and much lower for dormant $BCL_1$ and normal B cells (23 and 15 molecules/cell, respectively). Therefore, the expression of c-myc largely mimics the proliferative status of the cells.

In contrast to c-myc, the amount of product derived from c-fos mRNA (middle panel) does not correlate with proliferative status; it is low in both tumorigenic $BCL_1$ and normal lymphocytes (16 molecules/cell, in each), but high in the dormant $BCL_1$ population (110 molecules/cell). These findings are consistent with previous studies showing that anti-sIg treatment of neonatal B cells and a murine B cell tumor line with immature phenotype is associated with induction of c-fos expression and inhibition of proliferation (Monroe, 1988).

The data concerning c-fos expression suggests that this gene plays a critical role in inducing cell cycle arrest, and that its expression has been uncoupled from entry into the cell cycle. Antibody binding to cell surface Ig is proposed to activate a signal transduction pathway which leads to the upregulation of c-fos mRNA and the induction of cell cycle arrest. Since the c-fos gene product functions as a transcription activator in conjunction with Jun family members, its induction in CCALC suggests that dormancy is an active process, rather than the lack of a positive growth signal. Further preliminary analyses indicate that the level of c-jun mRNA is also significantly higher in CCALC than malignant or normal B cells. This supports the concept of an active role for fos in cell cycle arrest and suggests that Fos acts as an AP-1 complex with c-jun. It is possible that other AP1 transcription factors will also actively induce tumor cell cycle arrest.

EXAMPLE III

DORMANCY INDUCTION

1. Mechanism of Dormancy Induction

The above data do not indicate which branch(es) of the immune system, cellular or humoral, is necessary for induction of dormancy. To address this issue, the inventors examined the induction of dormancy in SCID mice which lack both T and B cells. Importantly, it was found that 18 of 19 SCID mice developed dormancy after receiving weekly injections of polyclonal murine anti-Id antibodies (50 μg/injection) over a period of 4–11 weeks, and challenged with $BCL_1$ after the first injection of antibody.

Figure 4:
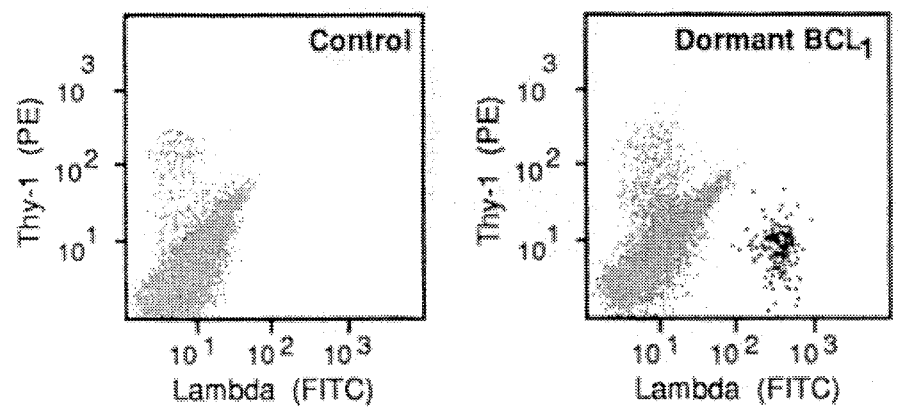
FIG. 4. Detection of CCALC in SCID mice passively immunized with anti-Id. Splenocytes from a normal SCID mouse, and a clinically stable, passively Id-immune SCID mouse challenged 70 days before with 5×10$^4$ BCL$_1$ cells were analyzed for their expression of Thy11 vs. $\lambda$. 10,000 events, gated to exclude non-viable cells, are shown for each plot. The $\lambda^+$/Thy1$^-$ population (absent in the control mouse) is colored red with the remaining cells gray.

FACS analysis of splenocytes from SCID mice, control or containing CCALC, is depicted in FIG. 4. In normal SCID mice, no $\lambda^+$ cells are found, reflecting the inability of these mice to produce mature B cells as a result of their lack of V-D-J recombination activity. The small number of $Thy1^+$ cells probably reflect the presence of NK cells in the SCID spleen. A SCID animal with dormant tumor was sacrificed 70 days after challenge with $BCL_1$ and analyzed for the presence of tumor cells. A distinct population of $\lambda^+$ cells was present in the spleen of this animal. These cells were the only cells which also stained with an anti-κ reagent, indicating that the $BCL_1$ cells had bound the passively administered anti-Id antibody, and that no normal B cells arising from the SCID host were present in the spleen.

These results represent a particularly important finding of the present invention in that they demonstrate, for the first time, the ability of antibodies to induce a clinical state of dormancy in the complete absence of T cells. This finding extends the observations of George et al (1987) that injection of anti-Id into normal mice later challenged with $BCL_1$ could induce dormancy. These results do not exclude the possibility that cellular immunity plays some role in the BALB/c Id-immune model, but indicates that humoral immunity may be sufficient. In a different murine lymphoma model of dormancy, Wheelock et al (1981) have shown that specific T lymphocytes and recruited macrophages that kill tumor cells in the peritoneal cavity are the critical effector mechanisms. The use of the SCID model will allow the investigation of the interaction between cellular and humoral immunity in the induction of tumor dormancy in a well-defined system.

2. Loss of Dormancy in Id-Immune Mice

Figure 5:
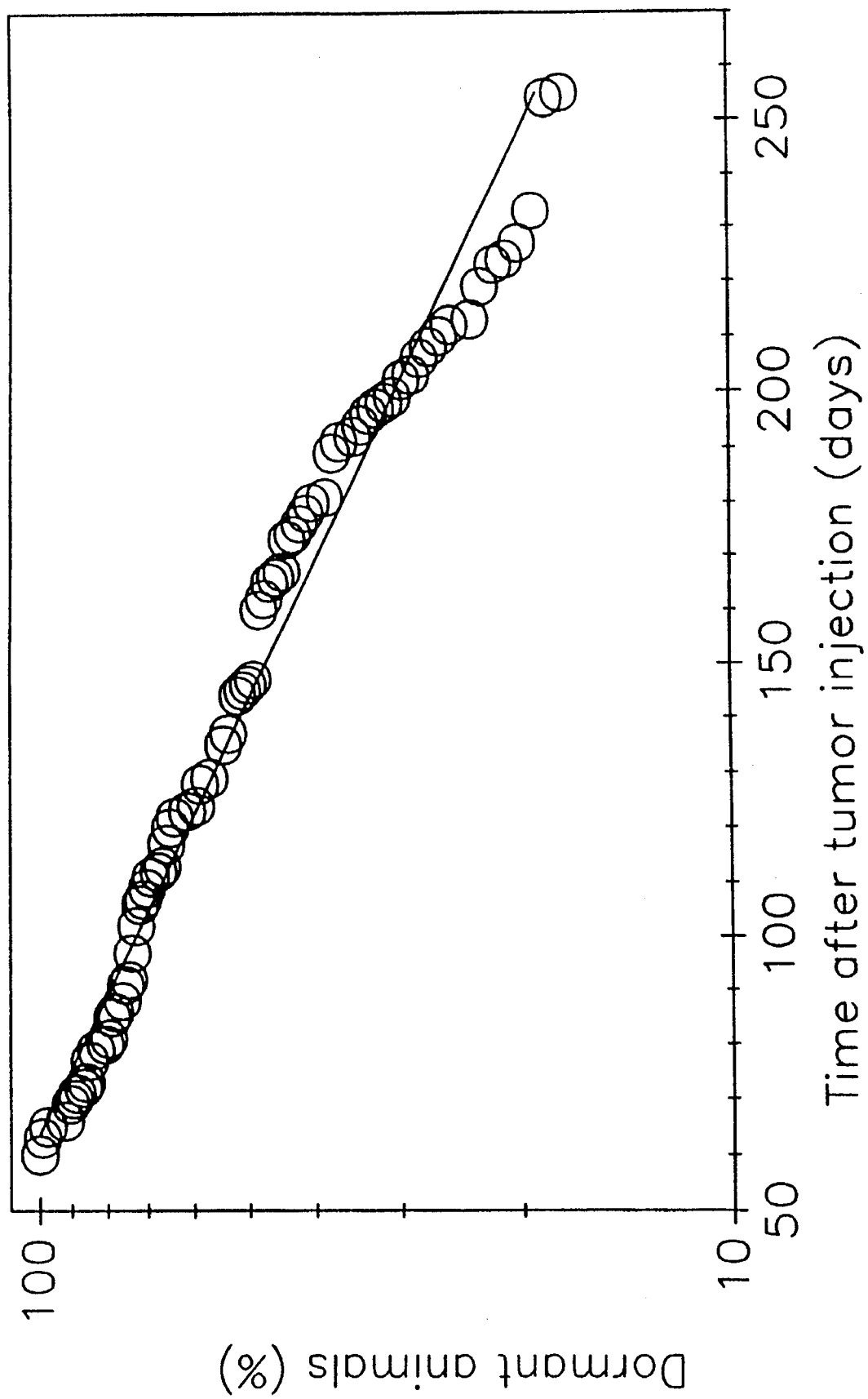
FIG. 5. Loss of dormancy with time after BCL$_1$ challenge. 114 dormant mice were examined weekly by palpation for splenic enlargement (Uhr et al., 1991). The graph was generated by computer analysis of the data with a regression coefficient of 0.988.

BALB/c mice progressively lose dormancy as evidenced by the appearance of splenomegaly and increasing numbers of $Id^+$ spleen cells indistinguishable by flow cytometry from growing $BCL_1$ cells. The rate of loss between 60 and 255 days after $BCL_1$ challenge is relatively constant (FIG. 5). This observation is reminiscent of the rate of recurrence of breast cancer which does not appear to change between 10–20 years post-mastectomy (Henderson et al., 1989). This strong correlation is a particularly important finding which indicates that studies such as these have direct relevance to the treatment of human patients.

These kinetics suggest that escape may be due to a single stochastically determined event, perhaps mutation. CCALC descend from cells with a fully malignant phenotype and major abnormalities in karyotype; these genetically unstable cells have a high probability of further mutations. It would be predicted that most of the mutations allowing the CCALC to regrow (escapees) would not involve the Id. Thus, with polyclonal antibody holding CCALC in check, several Id-epitopes would need to be eliminated to render the antibodies ineffective. This prediction was verified by the finding that in 21 of 27 mice that had lost dormancy, the escapees were Id$^+$ and transferred Id$^+$ BCL$_1$ tumor to recipients. The remaining 6 mice had low percentages of Id$^+$, $\lambda^+$ cells in their spleens and these escapees could represent sIg$^-$ variants.

To determine whether escapees are mutants that are resistant to induction of dormancy by Id-immunity, escapees from 2 mice (80 days after BCL$_1$ challenge) were injected into 23 Id-immune mice. Only 22% of the recipients became dormant, as compared to 72% of Id-immune mice receiving growing BCL$_1$ cells. These results indicate that the escapees were significantly less susceptible to the induction of dormancy than wild-type BCL$_1$ cells. Thus, escape from dormancy may arise from a genetic change in the slowly replicating population in which the elements involving signal transduction from sIg to the dormancy phenotype are mutationally altered. This explanation is consistent with both the steady rate of dormancy loss that suggests a stochastic process and the failure of reimmunization with BCL$_1$-Ig at 60 days to postpone escape.

Hence, the results presented herein demonstrate that the 3 BCL$_1$ populations under study, BCL$_1$ tumor, CCALC and escapee, are each different. There are ligand-induced physiological differences between BCL$_1$ tumor and CCALC, whereas, at least a portion of the escapees are genetically different. The most intriguing finding is that a cell with a fully malignant phenotype can be brought under growth restraint in vivo, and that restraint is so effective that mutation of tumor cells may be a common, if not necessary event for their escape.

EXAMPLE IV

THE DESIGN OF THERAPEUTIC STRATEGIES

To allow the more rapid development of further work, the inventors have established a BCL$_1$ line, 3B3, that replicates every three days in vitro and which is tumorigenic. This particular cell line grows slightly faster than in vivo passaged BCL$_1$ but is fully susceptible to induction of dormancy when BCL$_1$ is injected into either Id-immune or SCID mice receiving rabbit anti-Id antibody. The 3B3 in vitro cell line will be especially useful for investigating the kinetics of gene induction following anti-Ig treatment, and will facilitate the introduction of DNA constructs, by transfection and subsequent selection, to investigate the role of oncogene expression in dormancy induction.

It was important to establish that the phenotype of the in vitro cell line had not been altered as a result of cloning, especially with regards to malignant growth and dormancy induction in vivo. $10^4$ 3B3 cells were injected into several normal Balb/c and Id-immune mice and followed for tumor growth by splenic palpation. All of the normal Balb/c recipients exhibited gross splenomegaly, whereas 50% of Id-immune mice survived beyond 60 days with no evidence of splenomegaly. Two of these mice were sacrificed and the spleen examined for evidence of BCL$_1$ cells by FACS analysis. Cell cycle arrested tumor cells which stained with both anti-1 and anti-k reagents were readily detectable. These results established that the in vitro cell line is able to grow malignantly in naive recipients, and is also susceptible to cell cycle arrest induction in a manner similar to its BCL$_1$ parent.

On testing the effects of several anti-Ig reagents on $^3$H thymidine incorporation in cultured 3B3 cells, cell viability was found to remain unaffected for 72 hours indicating that cell cycle arrest and not cell death was responsible for the inhibition of DNA synthesis. The effects of different anti-Ig treatments on the proliferation of 3B3 in vitro was measured by the incorporation of $^3$H-thymidine. It was found that whilst all antibody preparations which interact with surface Ig on the 3B3 cells inhibited thymidine incorporation, there were considerable differences in the magnitude of the responses.

By far the strongest anti-proliferative signal was given by affinity-purified rabbit anti-Id. Several mechanisms are possible to explain this effect: 1) the rabbit antibody preparation contains a large proportion of antibodies with higher affinity as compared to the other antibody preparations; 2) the fact that the rabbit preparations is polyclonal and would recognize several epitopes on the surface Ig molecules might facilitate crosslinking; or more likely 3) rabbit antibodies are known to bind tightly to mouse Fc receptor, which might also play a role in this signal transduction pathway. It is thus clear that an arresting signal can be delivered to the 3B3 cells in vitro in a similar fashion to the dormancy inducing signal in vivo.

The availability of such a cell line therefore opens up new possibilities for future studies. A preferred strategy is considered to be to perform in vitro experiments utilizing the tumorigenic BCL$_1$ line, 3B3, to determine the optimal conditions under which selective ligands for cell surface receptors, such as monoclonal antibodies, will induce cell cycle arrest. Since the in vitro experiments may be conducted in 96-well plates, an enormous variety of conditions, doses, and the like may be examined and the results obtained in 1 to 3 days. The results will enable highly focused in vivo studies to be planned, which are naturally more expensive, labor intensive and time consuming. In vivo experiments may utilize SCID mice where the minimum assay for dormancy is the induction of small tumor cells 3 weeks after BCL$_1$ challenge. However, clinical dormancy, i.e., lack of splenomegaly for 60 days will continue to be the preferred standard.

In one series of studies, CCALC will be exposed in vitro to individual immunotoxins and chemotherapeutic agents and then transferred to naive recipients to determine which are the optimal agents in these 2 classes of pharmaceuticals. Immunotoxins used will be monoclonals linked by a heterobifunctional cross linker containing a hindered disulfide bond (SMPT) to deglycosylated ricin A-chain. In such studies, CCALC will be incubated with ITs at concentrations as low as $10^{-12}$M for 96 hours in order to obtain optimum killing. Controls are proposed to include an isotype-matched antibody of irrelevant specificity and an IT-A and antibody alone.

Chemotherapeutic agents proposed for early investigation include cyclophosphamide, an alkylating agent; doxorubicin a DNA intercalator and generator of free radicals; vincristine, which inhibits microtubule formation; bleomycin which breaks DNA shrouds; prednisone, which is lymphotoxic and which possibly induces apoptosis; and methotrexate, which interferes with DNA synthesis. After determining which IT(s) and chemotherapeutic agent(s) give maximum killing at 40% of the LD$_{50}$, a combination of these 2 types of reagents may be examined to determine if increased killing is obtained. From past experience with ITs, and chemotherapy, it is envisioned that 1–3 reagents from each class should suffice to give optimal results. Indeed, it is likely that only one IT will be used since each candidate is directed to surface Ig. The inventors predict the potentiation of IT by chemotherapy.

It is contemplated that, in such a manner, optimal killing by a combination of immunotoxins and chemotherapy may be established. The next series of studies will determine the cytotoxicity of these agents in vivo, using the in vitro results as a guide to in vivo dosages. It is possible, although not likely, that in vivo killing could be more effective than in vitro killing because of additional variables not present in the in vitro interactions, such as the presence of NK cells and monocytes. However, the in vivo doses may need to be increased relative to the in vitro studies due to considerations such as access to tumor cells and inability to maintain peak plasma concentrations of IT.

In the in vivo studies mice harboring CCALC will be treated with the cytotoxic regimen and assayed for optimal killing by flow cytometric analyses of their spleens and by cell transfer to secondary recipients. It is contemplated that appropriate doses will be in the order of 40% of the $LD_{50}$ of the chemotherapeutic agent(s) and 40% of the $LD_{50}$ of the IT(s). Problems of increased toxicity on combined use is not anticipated as ITs do not have the same side effects as chemotherapy, i.e. ITs do not damage bone marrow, liver, lungs or heart. The dose-limiting side effect of IT in humans is vascular leak syndrome. The relationship of the concentration of IT used in vitro to the blood levels in mice in vivo can be predicted accurately because of prior pharmacokinetic studies.

In these studies, it will be important to determine if the injected IT has bound to the tumor cells. This may be precisely accomplished by determined the ratios of $\lambda$ to rabbit Ig using flow cytometry and affinity purified reagents in the following way: If rabbit anti-μ-dgA is the IT used, then rat anti-mouse Id will be used to detect the CCALC and goat anti-rabbit Ig (absorbed with rat and mouse Ig) will be used to detect the IT. The ratio of rabbit Ig to rat Ig will determine the receptor occupancy. It can therefore be ascertain whether in vivo tumor cells undergo the same extent of interaction with IT as these do in in vitro.

The question of whether activated CCALC are more suspectable to cytotoxicity by the above regimen may be readily studied, both in vitro and in vivo, using mitogens such as LPS and dextran sulfate. At first glance, this could be considered counter productive since the major objectives of these studies are to determine how to either kill cell cycle arrested tumor cells, or to maintain such cells in their arrested state. Thus, stimulation of CCALC to active replicating cells be antithetical to the major objective. On the other hand, studies such as these would determine whether CCALC might be more readily/fully killed if they have been stimulated to replication.

To conduct such studies the inventors contemplate using a combination of 2 potent B cell mitogens that asinogyze in their mitogenic activity. Initially, cells in vitro will be stimulated for 24 to 48 hours with the mitogen combination using greater dosages of mitogen to determine which are most effective in activating pharmodene incorporation. The optimal concentration of mitogens will be followed by the optimal combination of immunotoxin-chemotherapy, and the cells transferred into naive recipients and id-immune recipients. Thus, if the activated CCALC are killed more readily than CCALC and yet the residual cells can be put into dormancy by id-immunity, it is possible that this more complex scenario could be used in vivo.

It is also contemplated that other pharmaceutical agents may maintain dormancy of cells not killed by cytotoxic agents. This will be examined by analyzing three further classes of compounds. Firstly, cytokines will be tested, particularly γIFN and TGF-β, as both have been reported to induce cell cycle arrest in vitro. The second class of compounds contemplated for use includes compounds known to induce terminal differentiation accompanied by cell cycle arrest. This includes polar/apolar compounds such as hexamethylene bisacetamide that can induce differentiation of several transformed cell lines and retinoic acid that causes terminal differentiation in human promyelocytic leukemia, resulting in dramatic remissions in patients with far-advanced disease. Thirdly, a wide variety of agents that interfere with signal-transduction will also be examined.

The question of receptor occupancy is important for clinical applications. The persistence of clinical dormancy in SCID mice as long as two months after discontinuation of passive antibody therapy suggests that continued receptor occupancy may not be necessary. This would suggest that arrested cells have been programmed to be in irreversible cell cycle arrest. This increases the prospect of successful human treatment regimens employing relatively lower doses and less frequent administration of therapeutic agents.

The inventors plan to more precisely determine the correlation between receptor occupancy and cell cycle status in the following manner. Graded numbers of sorted small lymphocytes that are not dividing (considered fully arrested) will be transferred to recipients, along with CCALC that are larger in size and appear to be dividing at a slow rate, and growing $BCL_1$. The inventors predict that small CCALC will not transfer tumor, but that larger CCALC will be able to transfer growing tumor but not as effectively as wild-type $BCL_1$. In addition to monitoring the recipients of the cell transfer for progressive splenomegaly, their spleens will also be examined to determine if they contain CCALC. Thus, CCALC may be present in the spleens of the recipients but remain dormant. If CCALC are present in these naive recipients, they will be followed to determine whether CCALC persist, die or eventually escape from dormancy. Again, the strategy will be to utilize in vitro data to perform a more limited number of in vivo experiments As discussed earlier, cell cycle arrest in Id-immune mice challenged with $BCL_1$ is more profound and long lasting than in SCID or BALB/c mice receiving large amounts of murine polyclonal anti-Id. There are 2 major possibilities to be considered. Firstly, the anti-Id levels in recipient mice are not maintained at sufficiently high levels to maximize dormancy, or secondly, $T_C$ or $T_H$ cells may potentiate the effect of anti-Ig in inducing dormancy. Preliminary results indicate that tumor immunity to $BCL_1$, as evidenced by delay in the onset of splenomegaly and death, can be transferred to BALB/c recipients using splenic T cells from Id-immune mice. However, it must be stressed that the results presented herein demonstrate that antibody treatment alone is still sufficient to induce cell cycle arrest.

To investigate the role of T cells, the inventors plan to transfer immune T cells, subsets of T cells and clones of T cells specific to $BCL_1$ to SCID mice some of which will be treated with rabbit anti-Id. Subsets of T cells can be obtained by magnetic bead removal of B cells, macrophages, NK cells (by anti-asialo GM), $CD4^+$ or $CD8^+$ cells. Purification of such populations can be verified by flow cytometry with appropriate antibodies. The inventors have generated 7 clones of $BCL_1$-specific T cells to date that are either $T_{H1}$ or $T_{H2}$ as judged by cytokine secretion.

Evidence that specific tumor immunity plays a role in keeping cancer under control comes from a large array of experimental and clinical observations, including the finding that immunosuppression correlates with both increased incidence and recurrence of some, but certainly not most, tumors (Penn et al., 1988). In the vast majority of experimental models of anti-cancer immunotherapy, cellular immunity is the major effector mechanism (Greenberg, 1991). Antibody-mediated immunotherapy has been shown to be effective in a few instances, most notably the treatment of B lineage lymphomas (Meeker et al., 1985) or myelomas (Lynch et al., 1972; Chen et al., 1976), but has not been efficacious in most epithelial tumors (Catane et al., 1988). The ineffectiveness in the latter instance may be caused by the inability of antibodies to penetrate such solid tumors (van Osdol et al., 1991; Baxter & Jain, 1991).

The question arises whether the $BCL_1$ cell cycle arrest model of the present invention represents control of tumor growth by conventional immunologic effector mechanisms or whether it represents a more generalizable phenomenon of a tumor-specific agonist mimicking a ligand-receptor interaction normally involved in growth or differentiation regulation. Evidence for the agonist mechanism in the presently described tumor model is: 1) $BCL_1$ cells are present in substantial and stable numbers in dormant spleen(s), i.e., the tumor cells have not been destroyed by an active immune response. 2) CCALC are physiologically different from growing $BCL_1$ tumor cells. 3) Escapees usually retain their tumor-specific antigen (Id) yet can be resistant to reinduction of dormancy.

Taken together, these data suggest that the genetic alterations leading to the changes in growth regulation and differentiation that characterize the malignant phenotype can be stably reversed by activation of the appropriate signal transduction pathways. The inventors propose that such signals likely act to by-pass or "override" the molecular lesion leading to the malignant phenotype, and allow the cell to once again express its normal phenotypic program. However, this state does involve a balance between the original genetic lesion and the countermanding signals, so additional mutations or perhaps even alternative signals may shift this balance back towards the malignant phenotype.

In the $BCL_1$ model, signals stemming from ligation of surface immunoglobulin by anti-Id antibodies, a natural signal transduction mechanism of B-lineage lymphocytes (Page & DeFranco, 1990; Cambier et al., 1991; Scott et al., 1991), can induce tumor cell cycle arrest. As this is an interaction of a tumor-specific agonist with a cell surface receptor, this renders the present invention widely applicable to the treatment of many different cancers. Indeed, in non-lymphoid cell-types, other cell surface molecules serve as links between the external environment and gene expression. Essentially all classes of cytokines and of cell or matrix adhesion molecules transduce signals from the outside of the cell to the nucleus and thereby influence all facets of cellular physiology. Thus, the phenomenon of cell cycle arrest, demonstrated here for a lymphoid malignancy, is likely to be generalizable to all forms of malignancy. A tumor of any given cell type will express one or more cell surface signal transduction receptor(s) that have the potential to override their growth and differentiation defect.

The retinoic acid-induced differentiation of F9 teratoma cells is associated with growth arrest (Strickland & Mahdavi, 1978), induction of c-fos and inhibition of c-myc expression (Mason et al., 1985; Whitman et al., 1990). In fact, the most extreme form of "dormancy" may be the observation that placement of teratocarcinoma cells into a normal blastula results in the incorporation of the tumor cells into the normal tissues of the developed organism (Mintz & Illmensee, 1975).

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodologY, techniques and/or compositions employed herein.

Baxter, L. T., Jain, R. K., *Micro. Res.* 41(1), 5 (1991).
Cambier, J. C., Morrison, D.C., Chien, M. M., Lehmann, K. R., *J. Immunol.* 146, 2075 (1991).
Catane, R., Longo, D. L., *Isr. J. Med. Sci.* 24, 471 (1988).
Chen, Y., Yakulis, V., Heller, P., *Proc. Soc. Exp. Biol. Med.* 151, 121 (1976).
Clarkson, B. D., Fried, J., Chou, T.-C., Strife, A., Ferguson, R., Sullivan, S., Kitahara, T., Oyama, A., *Cancer Res.* 37, 4506, 1977.
George, A. J. T., Tutt, A. L., Stevenson, F. K., *J. Immunol.* 138, 628 (1987).
Greenberg, P. D., *Adv. Immunol.* 49,281 (1991).
Henderson, J. C., Harris, J. R., Kinne, D. W., Hellman, S., in *Cancer: Principles and Practice of Oncology*, Jr. DeVita, V. J., S. Hellman and S. A. Rosenberg, Eds. (J. B. Lippincott, Philadelphia, 1989), p. 1201.
Kohler G., Milstein, C. *Nature* 256, 495 (1975)
Krikorian, J. G., C. S. portlock, D. P. Cooney, S. A. Rosenberg, *Cancer,* 46, 2093 (1980).
Krolick, K. A., P. C. Isakson, J. W. Uhr, E. S. Vitetta, *Immunol. Rev.* 48, 81 (1979).
Krolick, K. A., Uhr, J. W., Slavin, S., Vitetta, E. S., *J. Exp. Med.* 155, 1797 (1982).
Kubbies, M., Friedl, R., *Histochemistry* 83(2), 133 (1985).
Liu, C-M., Okayasu, T., Goldman, P., Suzuki, Y., Suzuki, K., and Wheelock, E. F., *J. Exp. Med.,* 164, 1259 (1986).
Lynch, R. G., Graff, R. J., Sirisinha, S., Simms, E. S., Eisen, H. N., *Proc. Natl. Acad. Sci. (USA)* 69, 1540 (1972).
Mason, I., Murphy, D., Hogan, B. L. M., *Differentiation* 30 76 (1985).
Meeker, T. C., Lowder, J., Cleary, M. L., Stewart, S., Warnke, R., et al, *N. Engl. J. Med.* 312, 1658 (1985).
Meltzer, A., *J. Surg. Oncol.* 43, 181 (1990).
Mintz, B., Illmensee, K., *Proc. Natl. Acad. Sci. (USA)* 72, 2585 (1975).
Monroe, J. G., *J Immunol* 140, 1454 (1988).
Page, D., DeFranco, A., *Mol. Cell Biol.* 10, 3003 (1990).
Penn, I., Brunson, M. E., *Transplant. Proc.* 20, 885 (1988).
Robinson, J. K., and Wheelock, E. F., *J. Immunol.* 126 673 (1981).
Scheuermann, R. H., Bauer, S. R., *Methods Enzymol.* 182 (1992) in press.
Scott, D. W., Borrello, M., Liou, L. B., Xiao-rui, Y., Warner, G. L., *Adv. Molec. and Cell. Immunol.* 1, (1991).
Slavin, S., S. Strober, *Nature* 272, 624 (1978).
Stevenson, F. K., A. J. T. George, M. J. Glennie, *Chem. Immunol.* 48, 126 (1990).
Strickland, S., Mahdavi, V., *Cell* 15(2) 393 (1978).
Terstappen, L. W. M. M., Mickaels, R., Dost, R., Loken, M. R., *Cytometry* 11, 506 (1990).

Trainer, D. L., and Wheelock, E. F., *Cancer Res.* 44 2897 (1984).

Uhr, J. W., Tucker, T., May, R. D., Siu, H., Vitetta, E. S., *Cancer Res.* 51, 5045S (1991).

van Osdol, W., Fujimori, K., Weinstein, J. N., *Cancer Res* 51, 4776 (1991).

Vitetta, E. S., Krolick, K. A., Miyama-Inaba, M., Cushley, W., Uhr, J. W., *Science* 219, 644 (1983).

Weinhold, K. J., Goldstein, L. T., and Wheelock, E. F., *J. Exp. Med.* 149, 732 (1979).

Wheelock, E. F., K. J. Weinhold, J. Levich, *Adv. Cancer Res.* 34, 107 (1981).

Whitman, M. M., Shen, Y.-M., Soprano, D., Soprano, K. J., *Cancer Res.* 50 3193 (1990).

What is claimed is:

1. A method for identifying tumor cells in cell cycle arrest comprising:

(a) obtaining a syngeneic population of cells from a patient suspected of having cancer;

(b) contacting said syngeneic population of cells with at least three monoclonal antibodies, each antibody being directed against a distinct cell surface molecule on tumor cells, under conditions effective to allow antibody binding;

(c) subjecting the contacted population of cells to multiparameter cell sorting to sort antibody bound tumor cells away from syngeneic non-tumor cells in said population; and (d) identifying, in the sorted population of tumor cells, the presence of tumor cells in cell cycle arrest.

2. The method of claim 1, multiparameter cell sorting comprises fluorescence-activated flow cytometry.

3. The method of claim 1, wherein step (d) comprises determining the DNA content of the tumor cells, wherein the presence of tumor cells with a DNA content corresponding to the $G_0/G_1$ cell cycle stage is indicative of tumor cells in cell cycle arrest.

4. The method of claim 3, wherein step (d) comprises identifying tumor cells which are in cell cycle stage $G_0/G_1$ and which are small in size.

5. The method of claim 1, wherein step (d) comprises determining the size of the tumor cells, wherein the presence of small sized tumor cells is indicative of tumor cells in cell cycle arrest.

6. The method of claim 1, wherein step (d) comprises determining the morphology of the tumor cells, wherein the presence of clumped chromatin, or the absence of conspicuous nucleoli, is indicative of tumor cells in cell cycle arrest.

7. The method of claim 1, wherein the syngeneic population of cells is obtained from a patient with a B cell tumor.

8. The method of claim 7, wherein the syngeneic population of cells is obtained from a patient with non-Hodgkin's lymphoma.

* * * * *

UNITED STATES PATENT AND TRADEMARK OFFICE
CERTIFICATE OF CORRECTION

PATENT NO. : 5,612,185

DATED : March 18, 1997

INVENTOR(S) : Johnathan W. Uhr, Ellen S. Vitetta, Louis J. Picker and Richard H. Scheuermann It is certified that error appears in the above-identified patent and that said Letters Patent is hereby corrected as shown below:

```
In claim 2, column 38, line 3, after "claim 1,", insert --
wherein the monoclonal antibodies are fluorescently labeled,
and the--.
```

Signed and Sealed this

Twenty-ninth Day of July, 1997

Attest:

BRUCE LEHMAN

*Attesting Officer*     *Commissioner of Patents and Trademarks*